(12) United States Patent
Hamada et al.

(10) Patent No.: US 8,702,947 B2
(45) Date of Patent: Apr. 22, 2014

(54) DEVICE AND METHOD FOR MEASURING MICROSPHERES

(75) Inventors: Ryo Hamada, Kanagawa (JP); Junya Suehiro, Fukuoka (JP)

(73) Assignee: Panasonic Corporation, Osaka (JP)

( * ) Notice: Subject to any disclaimer, the term of this patent is extended or adjusted under 35 U.S.C. 154(b) by 223 days.

(21) Appl. No.: 13/148,104

(22) PCT Filed: Feb. 5, 2010

(86) PCT No.: PCT/JP2010/000721
§ 371 (c)(1),
(2), (4) Date: Aug. 5, 2011

(87) PCT Pub. No.: WO2010/092773
PCT Pub. Date: Aug. 19, 2010

(65) Prior Publication Data
US 2011/0290649 A1    Dec. 1, 2011

(30) Foreign Application Priority Data

Feb. 10, 2009 (JP) ................................ P2009-028927

(51) Int. Cl.
*G01N 27/447* (2006.01)
*B03C 5/02* (2006.01)
*G01N 27/453* (2006.01)

(52) U.S. Cl.
USPC ....... 204/547; 204/643; 422/68.1; 422/82.01; 435/287.1

(58) Field of Classification Search
USPC ...................... 204/600, 547, 643; 435/287.1; 422/68.1, 82.01
See application file for complete search history.

(56) References Cited

U.S. PATENT DOCUMENTS 7,105,081 B2 * 9/2006 Gascoyne et al. ............ 204/547
2004/0226819 A1 11/2004 Talary et al.

(Continued)

FOREIGN PATENT DOCUMENTS

GB    2358473 A    7/2001
JP    11-501210 A  2/1999

(Continued)

OTHER PUBLICATIONS

Morgan et al; "AC Electrokinetics colloids and nanoparticles", Research Studies Press Ltd.,pp. 15-63, 2003.

(Continued)

*Primary Examiner* — Jennifer Dieterle
(74) *Attorney, Agent, or Firm* — Pearne & Gordon LLP

(57) ABSTRACT

A device and a method for measuring microspheres are provided in which, in a microsphere measurement of a sample liquid in which blood or saliva exists mixedly with microorganisms (included in the definition of the microspheres in the application) that are the detection object, both a dielectrophoretic trap at a high solution electric conductivity, and a highly sensitive and accurate impedance measurement can be attained. The microsphere measuring device includes: a cell 1 into which a liquid containing microsphere is to be introduced; at least one pair of electrodes 11a, 11b which are immersed in the cell 1; a dielectrophoresis power supply unit 4 which applies an AC voltage of a high frequency in the vicinity of 1 MHz, between the pair of electrodes 11a, 11b, thereby causing a dielectrophoretic force to act on the microspheres; a measurement unit 5 which applies an AC voltage of a low frequency in the vicinity of 10 kHz, between the pair of electrodes 11a, 11b, and which measures the impedance between the pair of electrodes 11a, 11b; and a control calculation unit 6 which calculates a time change of the impedance between the pair of electrodes 11a, 11b, and which calculates the number of the microspheres in the cell 1.

13 Claims, 19 Drawing Sheets

(56) References Cited

U.S. PATENT DOCUMENTS

| | | | |
|---|---|---|---|
| 2005/0118705 A1* | 6/2005 | Rabbitt et al. | 435/287.1 |
| 2006/0243594 A1* | 11/2006 | Schnelle et al. | 204/547 |
| 2007/0172939 A1* | 7/2007 | Xu et al. | 435/287.1 |
| 2010/0184115 A1* | 7/2010 | Lei et al. | 435/29 |
| 2010/0193358 A1* | 8/2010 | Hamada | 204/547 |

FOREIGN PATENT DOCUMENTS

| | | |
|---|---|---|
| JP | 2000-125846 A | 5/2000 |
| JP | 2001-204458 A | 7/2001 |
| JP | 2003-000224 A | 1/2003 |
| JP | 2003-024350 A | 1/2003 |
| JP | 2007-504952 A | 3/2007 |
| WO | 96/25998 A1 | 8/1996 |
| WO | WO 2008131609 * | 11/2008 |
| WO | 2009/037804 A1 | 3/2009 |

OTHER PUBLICATIONS

Suehiro et al; "Quantitative estimation of biological cell concentration suspended in aqueous medium by using dielectrophoretic impedance measurement method", j. Phys D: Appl. Phys. 32 (1999) pp. 2814-2820.

Dwe Allsopp et al; "Impedance technique for measuring dielectrophoretic collection of microbiological particles", J Phys. D: Appl. Phys 32 (1999) pp. 1066-1074.

International Search Report for PCT/JP2010/000721 dated May 18, 2010.

* cited by examiner

DEVICE AND METHOD FOR MEASURING MICROSPHERES

TECHNICAL FIELD

The present invention relates to a device and a method for measuring the number of microspheres in a sample solution by using dielectrophoresis, and more particularly to a device and a method for measuring microspheres in which an influence of the electric conductivity of a solution is avoided without performing pretreatment and which performs a measurement with a high sensitivity and a high accuracy.

BACKGROUND ART

Recently, it is particularly highly needed to rapidly, simply, and highly sensitively perform a quantitative measurement on microorganisms which may cause food poisoning or an infectious disease and which may cause any harm to the human body, because, in a step of producing food, a clinic unequipped with a microorganisms test facility, or the like, when a microorganisms test is performed on the spot, it is possible to prevent occurrence of food poisoning or an infectious disease.

In a so-called bio-sensor, when a biochemical substance in a sample is to be quantitatively measured by using artificial microspheres such as polystyrene labeled with a substance which is to be uniquely bonded to the measuring object, such as an antibody, it is necessary to quantitatively measure the number of microspheres in the sample or their bonding state. As described above, today, it is highly requested to rapidly, simply, and highly sensitively perform a quantitative measurement on microspheres contained in a liquid.

Here, the definition of the microspheres in the application will be described. The microspheres in the application are such as: polystyrene and the like substances, and particles in which any coating is applied to the substance; carbon nanotubes; metal particles such as gold colloids; and a living body or microspheres derived from a living body in a broad sense including small ones of so-called microorganisms, protozoans, and protozoas classified as a bacterium, a fungus, an actinomycete, a *rickettsia*, mycoplasma, or virus, larvae of organisms, cells of animals and plants, sperms, blood cells, nuclei acid, proteins, and the like. In addition, the microspheres in the application mean all particles which can be manipulated by dielectrophoresis. In the application, particularly, a measurement on microorganisms is assumed.

As the detection object in the application, particularly, microorganisms contained in blood and saliva of a human or an animal, or those collected from the surface of mucosa or the like to which blood or saliva of a human or an animal adheres are assumed. In blood and saliva of a human or an animal, ions are contained in high concentrations. This incurs a rise and variation of the electric conductivity of sample solutions, and causes a variation factor of a detecting method using dielectrophoresis.

Conventionally, the most widely used method of testing microorganisms is the culture method. In the culture method, a sample of microorganisms is smeared on a culture medium, the cultivation is performed under growth conditions for the microorganisms, and the number of colonies formed on the culture medium is counted, thereby quantitating the number of the microorganisms.

However, the colonization requires usually one to two days, or several weeks depending on the kind of microorganisms, and hence there is a problem in that the test cannot be rapidly performed. Furthermore, operations such as concentration, dilution, and smearing on the culture medium are necessary. Such operations must be performed by an expert. Consequently, there are problems in that the test cannot be simply performed, and that the accuracy is lowered by operational variations.

In order to solve the conventional problems, the inventor and other inventors have proposed a DEPIM (Dielectrophoretic Impedance Measurement) method in which dielectrophoresis and an impedance measurement are combined, as a rapid, simple, and highly sensitive method of counting the number of microorganisms (for example, see Patent Document 1).

In the DEPIM method, microorganisms are collected on microelectrodes by a dielectrophoretic force, and simultaneously an impedance change of the microelectrodes is measured, thereby quantitatively measuring the number of microorganisms in a sample liquid. Hereinafter, the measurement principle will be briefly described.

Usually, microorganisms have a structure where a cytoplasm which is ion-rich and high in dielectric constant and electric conductivity is surrounded by a cell membrane and cell wall which are relatively low in dielectric constant and electric conductivity, and can be deemed as dielectric particles. In the DEPIM method, a dielectrophoretic force which is a force acting, in a constant direction, on dielectric particles that are polarized in an electric field is used, and microorganisms which are dielectric particles are collected in the gap between the microelectrodes.

It is known that a dielectrophoretic force $F_{DEP}$ which acts on dielectric particles is given by following (Mathematical Formula. 1) (for example, see Non-patent Document 1). Hereinafter, description will be made while taking the case where dielectric particles are microorganisms, as an example.

$$F_{DEP} = 2\pi a^3 \in_0 \in_m Re[K] \nabla E^2 \qquad \text{[Mathematical Formula 1]}$$

where a: the radius of a microorganism in case of sphere approximation, $\in_0$: dielectric constant in vacuum, $\in_m$: relative dielectric constant of a sample liquid, and E: electric field intensity, and $\nabla$ is an operator indicating the gradient. In this case, $\nabla E^2$ shows the gradient of the electric field $E^2$, and means the degree of inclination of $E^2$ at the position, i.e., how steeply the electric field E spatially changes. Furthermore, K is called the Clausius-Mossoti factor, and indicated by (Mathematical Formula 2), and Re[K]>0 indicates positive dielectrophoresis in which the microorganisms move toward the high electric field region. Re[K]<0 indicates negative dielectrophoresis in which the microorganisms repelled from the high electric field region.

$$K = \frac{\varepsilon_b^* - \varepsilon_m^*}{\varepsilon_b^* + 2\varepsilon_m^*} \qquad \text{[Mathematical Formula 2]}$$

where $\in_b^*$ and $\in_m^*$ indicate the complex dielectric constants of the microorganisms and a solution, respectively. Usually, a complex dielectric constant $\in_r^*$ is indicated by (Mathematical Formula 3).

$$\varepsilon_r^* = \varepsilon_r - j\frac{\sigma}{\omega\varepsilon_0} \qquad \text{[Mathematical Formula 3]}$$

where $\in r$: relative dielectric constant of the microorganisms or the sample liquid, $\sigma$: electric conductivity of the microorganisms or the sample liquid, and $\omega$: angular frequency of the applied electric field.

From (Mathematical Formula 1), (Mathematical Formula 2), and (Mathematical Formula 3), it is seen that the dielectrophoretic force depends on the radius of a microorganism, the real part (hereinafter, indicated as Re[K]) of the Clausius-Mossoti factor, and the electric field intensity. Furthermore, it is seen that Re[K] is changed in dependence on the complex dielectric constants of the sample liquid and the microorganisms, and the frequency of the electric field.

In the DEPIM method, therefore, these parameters must be adequately selected, so that the dielectrophoretic force acting on the microorganisms is made sufficiently large and the microorganisms are surely collected in the electrode gap. The DEPIM method is characterized in that the electrical measurement is performed simultaneously with the microorganism collection to the electrodes by the dielectrophoresis, thereby quantitatively measuring the number of microorganisms in the sample liquid.

A microorganism has the above-described structure, and hence can be deemed as a microspheres which has electrically a specific impedance. When the number of microorganisms which are collected in the gap between the microelectrodes by dielectrophoresis is increased, therefore, the impedance between the electrodes is changed in accordance with the number of collected microorganisms.

Therefore, the inclination of a time change of the inter-electrode impedance has a value according to the number of microorganisms which are collected in the electrode gap per unit time, and the degree of the inclination corresponds to the concentration of the microorganisms in the sample liquid. When the inclination of a time change of the inter-electrode impedance is measured, consequently, it is possible to measure the concentration of the microorganisms in the sample liquid, or in other words the number of the microorganisms.

In the DEPIM method, furthermore, the number of the microorganisms is quantitated from the inclination of a time change of the impedance immediately after the start of dielectrophoresis, whereby the measurement of microorganisms is realized for a short time. In the above, the measurement principle of the DEPIM method has been briefly described. For details of the principle, please refer Non-patent Document 2.

The sample liquid which is used in the measurement in the application is assumed to be a liquid in which microorganisms collected by any method, such as blood or saliva is suspended in a liquid of a low electric conductivity and containing water as the principal constituent. It is seemed that, when microorganisms are collected, not only microorganisms but also ions contained in the vicinity are simultaneously collected. In this case, the dielectric constant of the sample liquid has a value which is substantially equal to that of water, with the result that the dielectrophoretic force acting on the microorganisms depends on the ion concentration of the sample liquid, or in other words the electric conductivity.

As the electric conductivity of a sample liquid is higher, usually, the dielectrophoretic force is smaller. In the case where it is assumed that a sample liquid such as described above is measured by the conventional DEPIM method, therefore, there is a problem in that, in a sample which has a high sample liquid electric conductivity, the dielectrophoretic force acting on microorganisms is reduced, and the number of microorganisms collected on microelectrodes is decreased, with the result that the measurement sensitivity is lowered. Moreover, the dielectrophoretic force acting on microorganisms is different depending on the sample liquid electric conductivity, and hence there is a problem in that, when sample liquids of different electric conductivities are measured, the dispersion of measurement results is large.

As means for solving the problems in a measurement of microorganisms or the like using dielectrophoresis, a technique is known in which, before a measurement, the sample liquid electric conductivity is reduced by ion exchange or the like. The technique is a method in which, before analysis, a sample liquid is treated in an ion-exchange column to reduce the sample electric conductivity, and thereafter microorganisms in the sample liquid are analyzed by dielectrophoresis (for example, see Patent Document 2).

Also a microorganism activity measuring device which, when the activity of microorganisms is to be measured, performs a rapid measurement in substantially real time to detect quantitatively and simply the activity of the microorganisms, and a microorganism activity measuring method which is used in the measurement are known. In the method, the kind of the microorganisms and the electric conductivity of a sample liquid are input, and a voltage (the amplitude and the frequency) which is optimum for measuring the activity is selected from Table 1 (for example, see Patent Document 3).

Furthermore, a measuring method is known in which, when dielectrophoresis and an impedance measurement are to be simultaneously performed, the voltage for inducing the dielectrophoresis and the voltage and frequency for performing the impedance measurement are respectively independently set. Typically, the voltage for performing the dielectrophoresis is set to 12 Vrms or higher and 1 kHz to 50 MHz, and that for performing the impedance measurement is set to 0.8 Vrms and 800 Hz (see Non-patent Document 3).

TABLE 1

| NAME OF MICROORGANISM | CONDUCTIVITY OF SUSPENSION | VOLTAGE | OPTIMUM FREQUENCY FOR MEASURING DEGREE OF ACTIVITY |
|---|---|---|---|
| *ESCHERICHIA COLI* | 0.1 mS/m | 3 Vpp | 1 MHz |
| *PSEUDOMONAS AERUGINOSA* | 0.1 mS/m | 3 Vpp | 5 MHz |
| *KLEBSIELLA PNEUMONIAE* | 0.1 mS/m | 3 Vpp | 10 MHz |

RELATED ART DOCUMENTS

Patent Documents

Patent Document 1: JP-A-2000-125846
Patent Document 2: JP-A-11-501210
Patent Document 3: JP-A-2003-000224

Non-Patent Documents

Non-patent Document 1: Hywel Morgan et al.: "AC Electrokinetics: colloids and nanoparticles", RESEARCH STUDIES PRESS LTD., published in 2003, pp. 15-63

Non-patent Document 2: J. Suchiro, R. Yatsunami, R. Hamada, M. Hara, J. Phys. D: Appl. Phys. 32 (1999) 2814-2820

Non-patent Document 3: D W E Allsopp et al. J. Phys. D: Appl. Phys. 32 (1999) PP. 1066-1074

SUMMARY OF THE INVENTION

Problem to be Solved by the Invention

Usually, manipulation of the microspheres using dielectrophoresis has a problem in that, when the electric conductivity of a sample liquid is raised, the positive dielectrophoretic force is reduced, and it is difficult to trap microspheres in an electrode gap. In order to solve the problem, it is necessary to perform dielectrophoresis at a relatively high frequency of 1 MHz or higher at which the change (reduction) of the dielectrophoretic force is small with respect to the rise of the electric conductivity of the sample liquid. Moreover, a dielectrophoretic force the level which is sufficiently large for measuring an impedance change must be induced, and hence the applied voltage must be made higher, with the result that the current flowing to electrodes is increased. In the case where the frequency is high and the measuring voltage (current) has a large amplitude as described above, the through rate becomes high, and hence it is usually difficult to perform the impedance measurement, because of performance limitations of devices of amplifier circuits and the like, so that the measurement accuracy is lowered. For an impedance measurement circuit, in conditions of a voltage for measuring the impedance, therefore, it is more advantageous as the amplitude is smaller and the frequency is lower. Namely, means for achieving both the trapping of microspheres to electrodes by means of dielectrophoresis, and a highly accurate impedance measurement is necessary.

In Patent Document 1, an example in which a sinusoidal AC voltage with a peak to peak voltage of 100 V at a frequency of 1 MHz is applied between flat plate electrodes is shown, and it is described that the frequency of the AC to be applied at this time can be arbitrarily selected from a frequency range where dielectrophoresis occurs. However, there is no suggestion about means for achieving both avoidance of the influence of the solution electric conductivity by selecting the frequency, and a highly accurate impedance measurement.

In the technique disclosed in Patent Document 2, pretreatment of ion exchange is necessary before the analysis by dielectrophoresis, and hence there are problems in that the simplicity of microsphere measurement is impaired, and that the whole measurement requires a prolonged period of time. Moreover, the electric conductivity of the sample liquid after the ion exchange treatment depends on that before the ion exchange treatment. Therefore, it is impossible to solve the problem in that dispersion of the electric conductivity among samples causes dispersion in results of microsphere measurement by using dielectrophoresis such as the DEPIM method.

In the microorganism activity measuring device of Patent Document 3, the kind of the microorganisms and the electric conductivity of a sample liquid are input, and a voltage (the amplitude and the frequency) which is optimum for measuring the activity is selected from the table. A frequency at which a difference is formed in the dielectrophoretic force depending on the activity state is selected.

In the technique disclosed in Non-patent Document 3, voltage conditions for respectively performing dielectrophoresis and the impedance measurement can be individually selected, and hence dielectrophoresis can be performed at a high frequency of 1 MHz or higher in which a change of the dielectrophoretic force is small with respect to a rise of the electric conductivity of a sample liquid. However, the technique has a problem in that, in a low frequency at which the impedance measurement is performed, the influence of the Warburg impedance becomes remarkable, the impedance measurement cannot be correctly performed, and the correctness of the measurement result is significantly impaired.

As an example which specifically shows the above-described influence of the Warburg impedance, there is a case where, in the technique disclosed in Non-patent Document 3, when the impedance measurement is not performed after the electric conductivity of a sample contained in one cell is made accurately coincident with that of the measuring object contained in the other cell, the degree of contribution of the electrode polarization is increased, and the correct impedance measurement may seriously impair the correctness of the measurement result.

In a sample liquid in which blood or saliva exists mixedly with microorganisms that are included in the definition of the microspheres in the application, and that are the detection object, when humans or animals from which a sample is to be collected, or times when the sample is to be collected are different, as described above, the electric conductivity is largely changed. In the technique disclosed in Non-patent Document 3, in the case where a sample liquid in which blood or saliva exists mixedly with microorganisms that are the detection object is to be measured, therefore, the electric conductivity of a sample contained in one cell must be made accurately coincident with that of the measuring object contained in the other cell. However, this is hardly realized. Therefore, the correct impedance measurement cannot be performed, and the correctness of the measurement result is significantly impaired.

The invention has been made in view of the above-described circumstances, and an object thereof is to provide a device and method for measuring microspheres in which, in the case where microorganisms contained in blood or saliva of a human or an animal, or those collected from the surface of mucosa or the like to which blood or saliva adheres are set as the detection object, and the solution electric conductivity of a sample liquid to be measured is high and varied in every sample, both a dielectrophoretic trap at a high solution electric conductivity, and a highly sensitive and accurate impedance measurement can be attained.

Means for Solving the Problem

The inventors have found that, when microspheres, particularly bacteria are to be subjected to dielectrophoresis, there is a frequency range where the influence of the solution electric conductivity can be avoided, and also that, aside from this, there are a frequency range and amplitude which are suitable for a highly accurate impedance measurement. The invention has been accomplished on the basis of this finding.

A microsphere measuring device of the invention includes: a cell into which a liquid containing microspheres contained in at least one of blood and saliva is introduced; at least one pair of electrodes immersed in the cell; a dielectrophoresis power supply unit configured to apply an AC voltage between the pair of electrodes; a measurement unit configured to measure an impedance between the pair of electrodes; and a control calculation unit configured to calculate a time change of the impedance between the pair of electrodes, and which calculates a number of the microspheres in the cell, and the control calculation unit instructs the dielectrophoresis power supply unit to apply an AC voltage of a first frequency and a second frequency between the pair of electrodes, the first frequency for inducing dielectrophoresis in the microspheres, the second frequency for measuring the impedance between the pair of electrodes and being higher than a frequency at which an influence of a Warburg impedance occurs.

According to the configuration, the AC voltage of the first frequency is applied to cause a dielectrophoretic force to act on the microspheres, and the AC voltage of the second frequency that is a frequency higher than the boundary frequency is applied to measure the impedance. Therefore, both a dielectrophoretic trap at a high solution electric conductivity and an impedance measurement with high sensitivity and high accuracy can be attained.

In the microsphere measuring device of the invention, the AC voltage of the first frequency has a first amplitude, and the AC voltage of the second frequency has a second amplitude.

According to the configuration, the AC voltage of the first frequency has the first amplitude, and the AC voltage of the second frequency has the second amplitude. Therefore, adequate voltages can be applied to dielectrophoresis and the impedance measurement, respectively.

In the microsphere measuring device of the invention, the second amplitude is smaller than the first amplitude.

According to the configuration, there is an effect of preventing the AC voltage of the second frequency for measuring the impedance from affecting dielectrophoresis.

In the microsphere measuring device of the invention, the control calculation unit adjusts at least one of the first frequency and the second frequency based on a solution electric conductivity.

According to the configuration, the first frequency and the second frequency are adjusted based on the solution electric conductivity. Even when the solution electric conductivity is varied, therefore, dielectrophoresis and the impedance measurement can be performed at an adequate frequency.

In the microsphere measuring device of the invention, the first frequency and the second frequency are sequentially switched.

According to the configuration, the first frequency and the second frequency are sequentially switched. Therefore, dielectrophoresis and the impedance measurement can be rapidly performed, and conditions which are optimum respectively for them can be selected.

In the microsphere measuring device of the invention, a time period for applying the AC voltage of the second frequency is shorter than a time period for applying the AC voltage of the first frequency.

According to the configuration, during the application of the AC voltage of the second frequency used for performing the impedance measurement, microspheres are not caused to be scattered from electrodes by a loss of dielectrophoresis force, and the microspheres can be surely trapped between the electrodes. Therefore, a highly sensitive measurement can be realized.

In the microsphere measuring device of the invention, the second frequency is higher than 800 kHz and lower than the first frequency.

According to the configuration, the microspheres are trapped at a high frequency, and the impedance is measured at a low frequency. Therefore, both a dielectrophoretic trap at a high solution electric conductivity and a highly sensitive and accurate impedance measurement due to the performance of the impedance measurement at a low frequency can be attained.

In the microsphere measuring device of the invention, the dielectrophoresis power supply unit superimposes and applies the AC voltage of the first frequency and the AC voltage of the second frequency between the pair of electrodes, the microsphere measuring device includes filter separation means for separating frequency components of the AC voltage of the second frequency from the superimposed AC voltages applied between the pair of electrodes, and the measurement unit measures the impedance between the pair of electrodes corresponding to the filter-separated frequency components of the AC voltage of the second frequency.

According to the configuration, the AC voltages of the first and second frequencies are superimposed and applied, frequency components of the AC voltage of the second frequency are filter-separated, and the impedance between the pair of electrodes is measured. Therefore, designing a measurement circuit can be simplified, and the cost can be lowered. Moreover, the superimposed application of the AC voltages of the first and second frequencies enables the trapping of microspheres and the impedance measurement to be simultaneously performed. Therefore, a phenomenon where, when the switching from the first frequency to the second frequency is performed, the dielectrophoretic force acting on the microspheres is reduced and the microspheres separate from the electrode gap can be prevented from occurring, and hence a highly sensitive and accurate measurement can be performed.

A microsphere measuring method of the invention is a method in which an AC electric field is applied between a pair of electrodes immersed in a sample liquid containing microspheres contained in at least one of blood and saliva, the microspheres are placed at a predetermined position by a dielectrophoretic force, and a number of the microspheres in the sample liquid is measured, wherein the method includes: a step of applying an AC voltage of a first frequency between the pair of electrodes to cause a dielectrophoretic force to act on the microspheres; a step of applying an AC voltage of a second frequency between the pair of electrodes, the second frequency for measuring an impedance between the pair of electrodes and being higher than a frequency at which an influence of a Warburg impedance occurs, and a step of measuring the impedance between the pair of electrodes; and a step of calculating a time change of the impedance between the pair of electrodes, and calculating a number of the microspheres in the cell.

According to the configuration, the AC voltage of the first frequency is applied to cause a dielectrophoretic force to act on the microspheres, and the AC voltage of the second frequency that is a frequency which is higher than the boundary frequency is applied to measure the impedance. Therefore, both a dielectrophoretic trap at a high solution electric conductivity and an impedance measurement with high sensitivity and high accuracy can be attained.

Moreover, the microsphere measuring method of the invention includes a step of selecting the first frequency and the second frequency based on a solution electric conductivity.

According to the configuration, the first frequency and the second frequency are selected based on the solution electric conductivity. Even when the solution electric conductivity is varied, therefore, dielectrophoresis and the impedance measurement can be performed at an adequate frequency.

Moreover, the microsphere measuring method of the invention includes: a step superimposing and applying the AC voltage of the first frequency and the AC voltage of the second frequency between the pair of electrodes; and a step of separating frequency components of the AC voltage of the second frequency from the superimposed AC voltages applied between the pair of electrodes, and measuring the impedance between the pair of electrodes.

According to the configuration, the AC voltages of the first and second frequencies are applied in a superimposed manner, frequency components of the AC voltage of the second frequency are filter-separated, and the impedance between the pair of electrodes is measured. Therefore, a measurement circuit can be simplifiedly designed and the cost can be lowered. Moreover, the superimposed application of the AC voltages of the first and second frequencies enables the trapping of microspheres and the impedance measurement to be simultaneously performed.

Advantages of the Invention

According to the invention, in a microsphere measurement in which microorganisms included in the definition of the microspheres in the application, such as blood or saliva are set as the measuring object, the AC voltage of the first frequency is applied to cause a dielectrophoretic force to act on the microspheres, and the AC voltage of the second frequency that is a frequency which is higher than the boundary frequency is applied to measure the impedance. Therefore, both a dielectrophoretic trap at a high solution electric conductivity, and a highly sensitive and accurate impedance measurement can be attained.

MODE FOR CARRYING OUT THE INVENTION

First Embodiment

Figure 1:
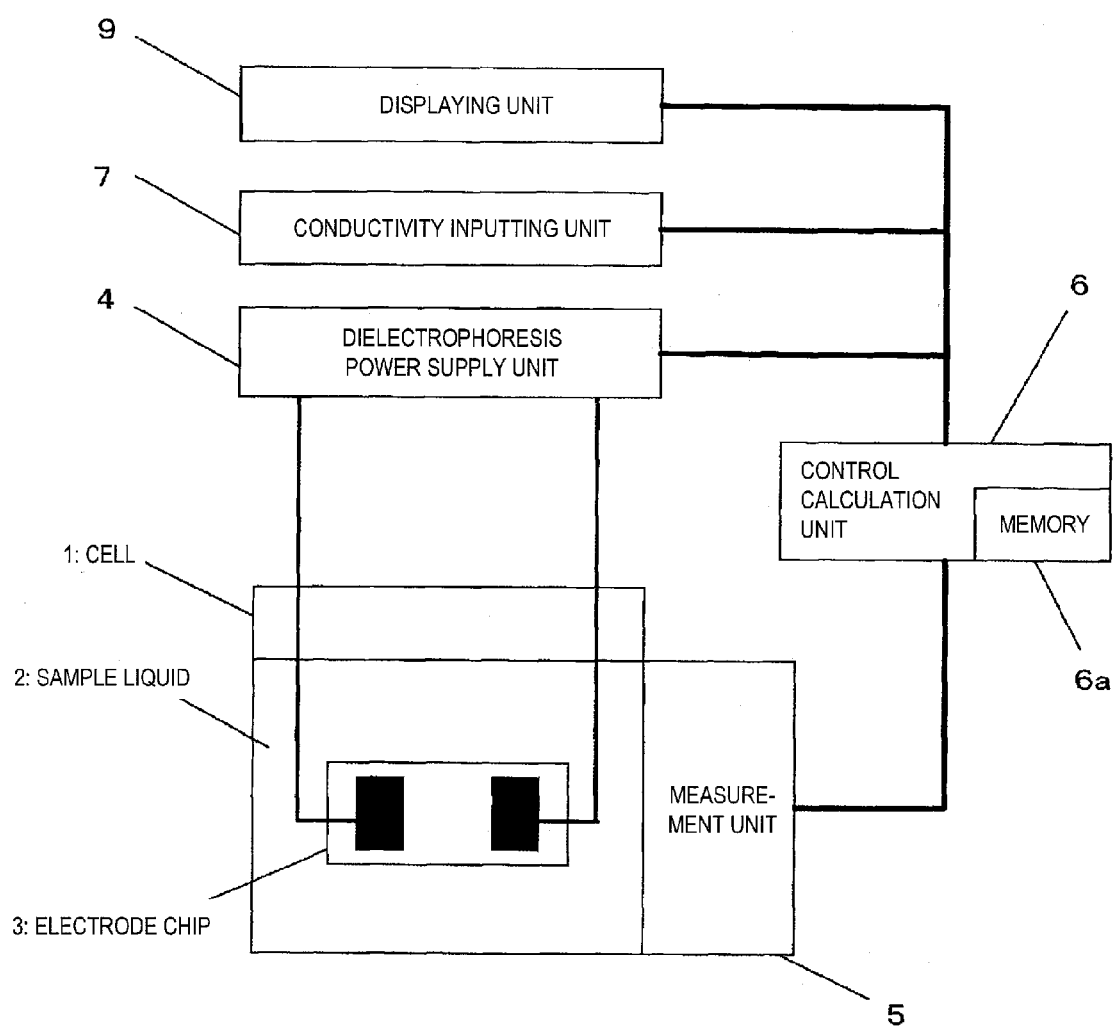
FIG. 1 is a schematic configuration diagram (1) illustrating a microsphere measuring device of a first embodiment of the invention.

Hereinafter, a microsphere measuring device of an embodiment of the invention will be described with reference to the drawings. FIG. 1 is a configuration diagram of the microsphere measuring device of the embodiment, and FIG. 2 is a schematic view illustrating an electrode chip of the microsphere measuring device of the embodiment.

Referring to FIG. 1, 1 denotes a cell which holds a sample liquid 2 containing microspheres to be measured, 3 denotes an electrode chip including an electrode pair which collects the microspheres by dielectrophoresis, 4 denotes a dielectrophoresis power supply unit, 5 denotes a measurement unit which measures a optical or electrical change caused by microspheres that are trapped by dielectrophoresis, 6 denotes a control calculation unit which performs a control on the whole microspheres measuring device, analysis calculation of measurement results, input/output processes, and the like, and 7 denotes a conductivity inputting unit for inputting the electric conductivity of the sample liquid 2.

Figure 2:
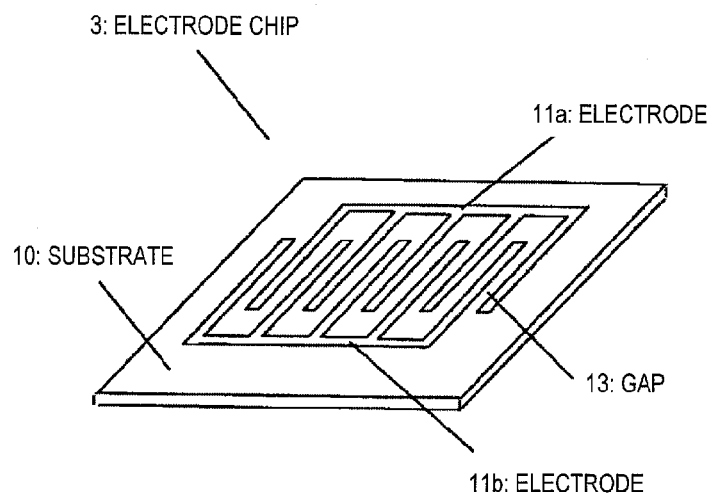
FIG. 2 is a schematic view illustrating an electrode chip of the microsphere measuring device of the embodiment of the invention.

Referring to FIG. 2, 10 denotes a substrate, 11a and 11b denote electrodes which are formed on the substrate 10, and which constitute a pair of poles, and 13 denotes an interelectrode gap between the electrode 11a, 11b. On the substrate 10, patterns of the electrode 11a, 11b are formed by an electrically conductive material such as a metal. Examples of a preferred material are gold, silver, copper, aluminum, and platinum. Preferably, the material has a sufficient electric conductivity. In the embodiment, silver is used.

Figure 3:
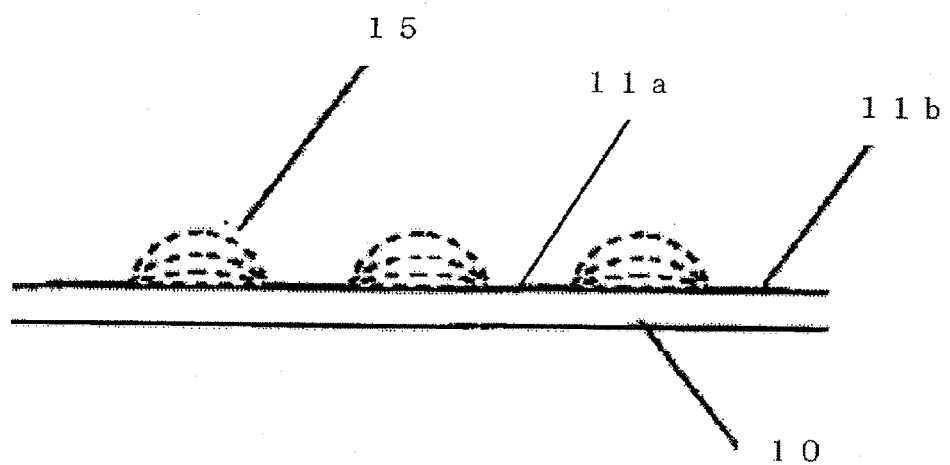
FIG. 3 is a view showing electric force lines 15 which are produced by a voltage applied between measurement electrodes 11a, 11b in the embodiment of the invention.

FIG. 3 shows electric force lines 15 which are produced by a voltage applied between the measurement electrodes 11a, 11b. In the embodiment, the configuration in the vicinity of the gap 13 between the measurement electrodes 11a, 11b corresponds to a high electric field region. In the portion, the electric field is most concentrated in the gap 13. In the gap 13, therefore, the microspheres experience dielectrophoretic force most strongly.

Preferably, each of the electrodes 11a, 11b is configured by a thin film which is sufficiently thin with respect to its width, and has a thickness of, for example, about 1,000 angstroms with respect to a width of 100 μm. According to the configuration, a non-uniform electric field is formed in an edge portion as viewed in the thickness direction, so that the microspheres can be efficiently subjected to dielectrophoresis.

A method of patterning the electrodes 11a, 11b is requested to form a desired pattern with a selected material. A usual process which is used for forming an electrode, such as a method in which a metal thin film is formed by sputtering, vapor deposition, plating, or the like, and a pattern is formed by photolithography, laser processing, or the like, and that in which a pattern is directly formed by, for example, printing may be selected. The most adequate process may be selected in view of the productivity, the cost, and the like. In the embodiment, a thin film of silver is formed by sputtering, and a pattern is formed by photolithography.

The electrodes 11a, 11b are connected to the dielectrophoresis power supply unit 4. The dielectrophoresis power supply unit 4 applies an AC voltage of a specific frequency between the electrodes 11a, 11b. In the specification, the AC voltage means a sinusoidal voltage, or in addition a voltage in which the flow direction is changed in a substantially constant period, and average values of currents in both directions are equal to each other. As described later, the frequency applied by the dielectrophoresis power supply unit 4 is adequately determined by the control calculation unit 6.

In a state where the electrode chip 3 is immersed in the sample liquid 2 and the electrodes 11a, 11b are contacted with the sample liquid 2, when the AC voltage is applied between the electrodes 11a, 11b, the microspheres contained the sample liquid 2 are captured by a dielectrophoretic force to the gap 13 interposed between the electrodes 11a, 11b.

Figure 4A:
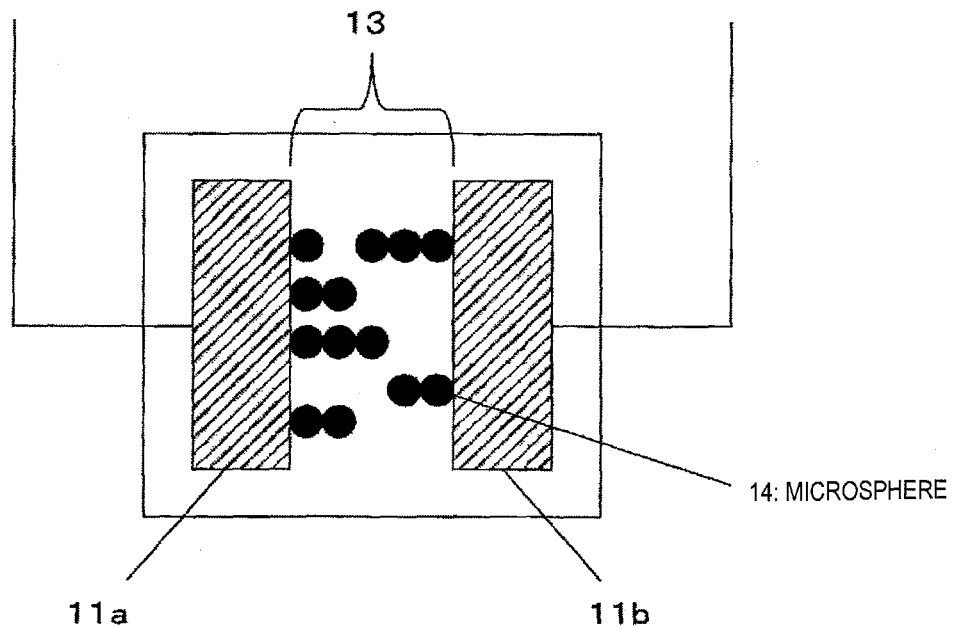
FIGS. 4(a) and 4(b) are diagrams illustrating a manner in which microspheres 14 are trapped to opposing edge portions of the electrodes 11a, 11b along the electric force lines.

In the case where a positive dielectrophoretic force acts on microspheres 14, as shown in FIG. 4(a), the microspheres 14 are trapped to the opposing edge portions of the electrodes 11a, 11b in the region of the gap 13 which is the high electric field region, along the electric force lines in the bead string shape which is called a pearl chain.

Figure 4B:
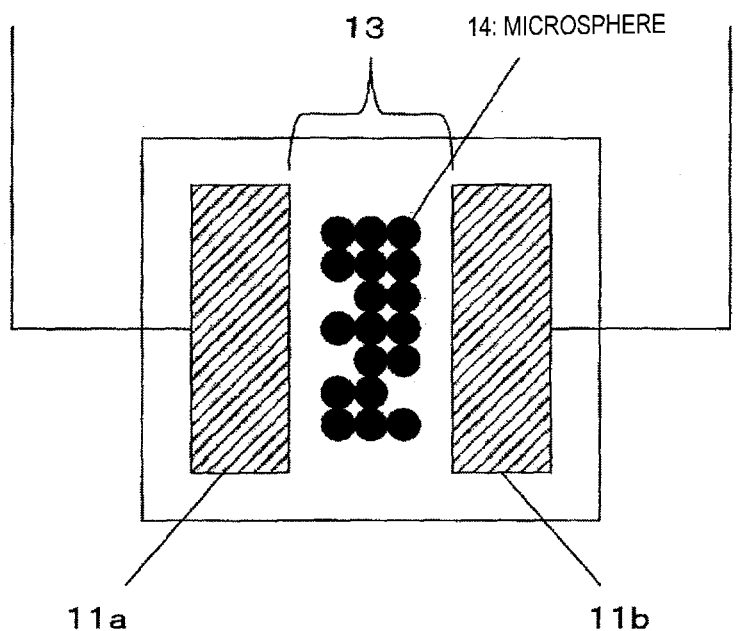

In contrast, in the case where a negative dielectrophoretic force acts on the microspheres 14, as shown in FIG. 4(b), the microspheres are trapped in the direction separating from the high electric field region, i.e., to the vicinity of the opposing center portions of the electrodes 11a, 11b in the region of the gap 13 which is the weak electric field portion.

Figure 5:
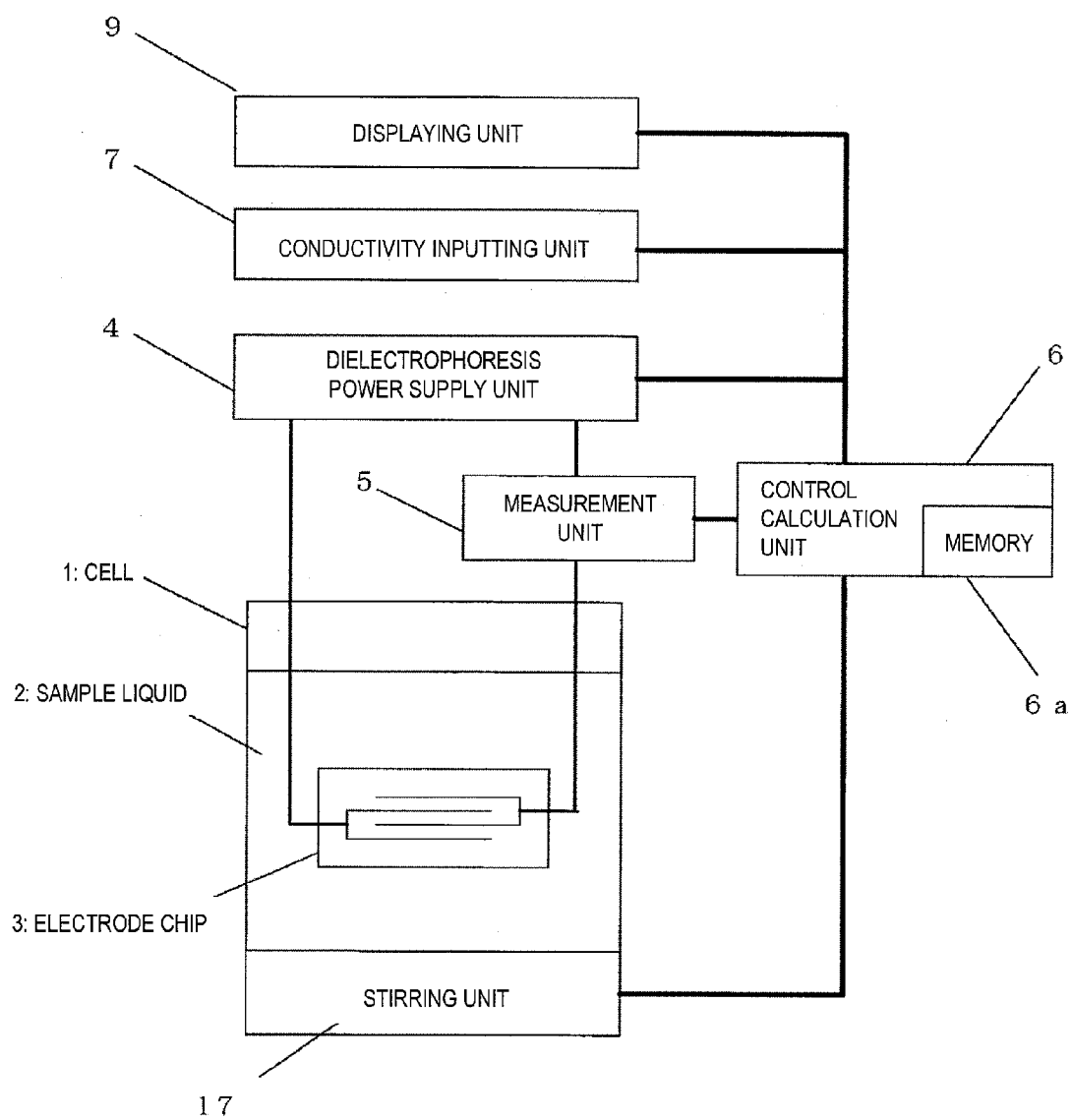
FIG. 5 is a schematic diagram (2) illustrating the microsphere measuring device of the first embodiment of the invention.

The measurement unit 5 measures an impedance change due to the microspheres which are trapped to the gap 13 as described above. Specifically, as shown in FIG. 5, the measurement unit 5 configures a circuit which measures the impedance between the electrodes 11a, 11b, between the dielectrophoresis power supply unit 4 and the electrode chip 3.

In this case, the measurement unit 5 is configured by a circuit which measures the value of a current flowing between the electrodes 11a, 11b, and a phase difference between the voltage and current that are applied by the dielectrophoresis power supply unit 4, and the like. The measurement unit 5 measures changes of the current between the electrodes 11a, 11b, and the phase difference which are caused by a phenomenon in which the microspheres are moved by dielectrophoresis to be concentrated in the vicinity of the high electric field region. In the above-described measurement of the current value, known methods such as that in which a detection resistor is placed in series to the electrodes and the voltage drop is converted to the current value, or a current-voltage converting circuit using a usual operation amplifier can be used.

The current value and phase difference which are measured by the measurement unit 5 are passed to the control calculation unit 6. The control calculation unit 6 calculates the value of the impedance between the electrodes 11a, 11b from the current, the phase difference, and information of the voltage and frequency which are applied by the dielectrophoresis power supply unit 4.

When the region which is between the electrodes 11a, 11b, and which is filled only with the sample liquid 2 before the voltage application is replaced with the microspheres of a different electric impedance by trapping due to dielectrophoresis, the impedance between the electrodes 11a, 11b is changed in accordance with the number of the trapped microspheres.

Therefore, the number of the microspheres trapped to the gap 13 can be estimated from the difference or in other words, from the change amount between the impedance value at a certain time and the initial impedance value immediately after the application of the voltage. The number of the trapped microspheres depends on the concentration of the microspheres contained in the sample liquid. Therefore, it is possible to measure the number of the microspheres in the sample liquid.

Figure 6:
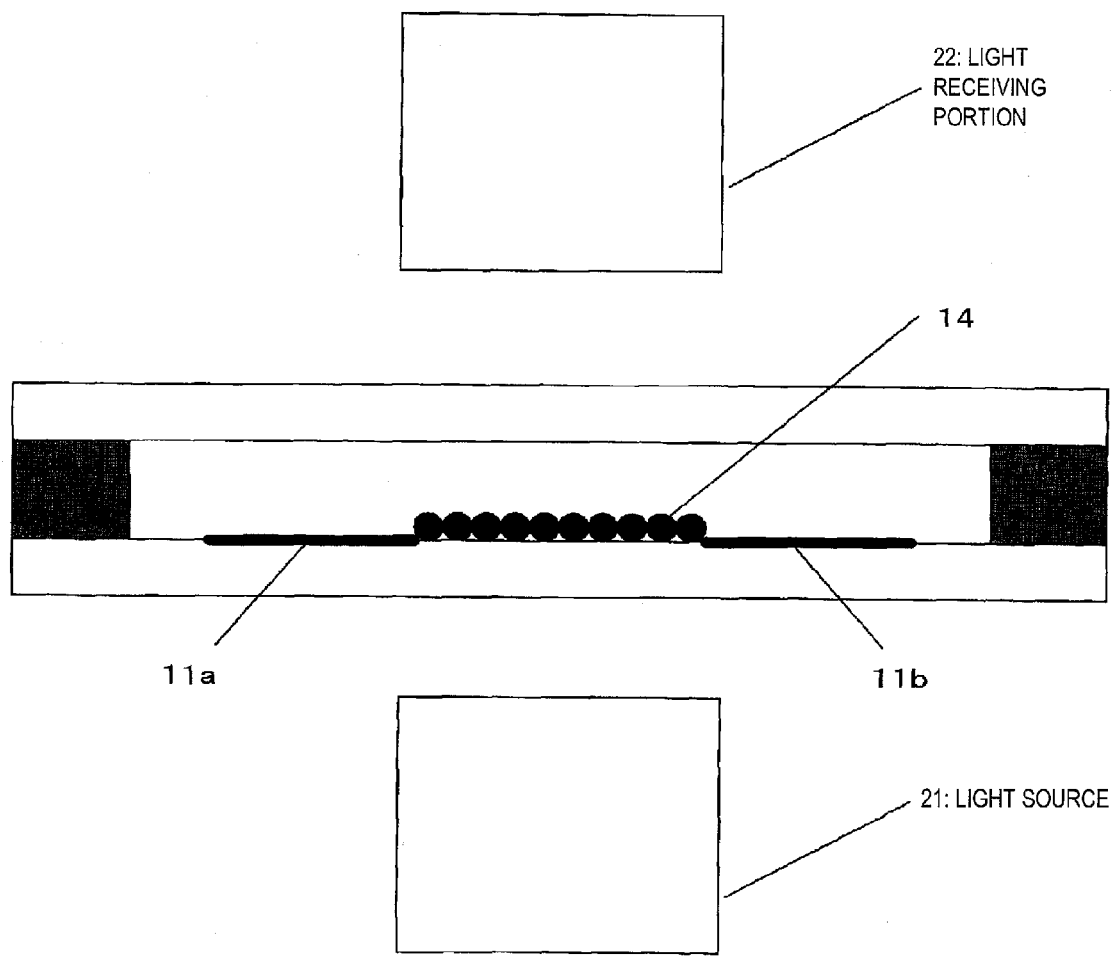
FIG. 6 is a schematic diagram (3) illustrating the microsphere measuring device of the first embodiment of the invention.

As shown in FIG. 6, the measurement unit 5 can be realized also by optical measuring means. In this case, the cell 1 is placed in a positional relationship in which the gap 13 is included in an optical path between a light source 21 and a light receiving portion 22. By using a phenomenon in which the amount of light incident on the light receiving portion 21 is changed in accordance with the number of the microspheres trapped to the gap 13, it is possible to estimate the number of the microspheres trapped to the gap 13.

Alternatively, information of the light receiving portion 22 may be passed to the control calculation unit 6 to be converted to an image, and the control calculation unit 6 may directly calculate the number of particles by using a particle determination algorithm or the like, or may convert the information to the number of microspheres by obtaining a microsphere area with respect to the view field area. The number of the microspheres trapped to the gap 13 and obtained in this way depends on the concentration of the microspheres contained in the sample liquid. Therefore, it is possible to measure the number of the microspheres in the sample liquid.

In order to trap the microspheres to the gap 13, as described above, it is necessary to induce a dielectrophoretic force which is sufficiently large with respect to all external forces acting on the microspheres other than dielectrophoresis, such as the viscous force, the gravitation, and the Brownian motion. When the force is insufficient, the number of microspheres which can be measured by the measurement unit 5 is reduced, and hence the measurement sensitivity and accuracy are remarkably lowered. When the signal level is lower than that which can be measured by the measurement unit 5, the measurement of microspheres cannot be performed.

In the embodiment, therefore, the control calculation unit 6 adequately determines a frequency at which a dielectrophoretic force that is sufficient for trapping microspheres to the gap 13 acts, and the dielectrophoresis power supply unit 4 applies a voltage of the determined frequency. This enables a signal which can be sufficiently detected by the measurement unit 5, to be taken out. Therefore, the concentration of the microspheres can be measured highly accurately and highly sensitively.

The control calculation unit 6 is configured by a CPU which is not shown, and circuits such as a memory 6a which stores programs defining the series of operations, and various data, and controls the series of measurement operations. The conductivity inputting unit 7 is configured so that the electric conductivity of the sample liquid can be input before measurement. For example, the means can be realized by a method in which a numerical value is input through a numerical keypad, or that in which one of switches respectively corresponding to a plurality of conductivity ranges such as "0 to 50 µS/cm" and "50 to 100 µS/cm" is pressed.

The memory 6a has a frequency selection table for selecting an adequate frequency of the voltage applied by the dielectrophoresis power supply unit 4 from the value of the electric conductivity of the sample liquid and given from the conductivity inputting unit 7. In the frequency selection table, the optimum frequency and value of the applied voltage at which a sufficient dielectrophoretic force acts on the microspheres are stored for each electric conductivity of the sample liquid 2 in the form of a table.

Here, the frequency selection table stored in the memory 6a will be described in detail. As shown in Table 2, at least the electric conductivity of the sample liquid, and the amplitude and optimum frequency of the applied AC voltage are stored in the frequency selection table while being correlated with each other. The table may be prepared while setting a specific numerical value or a certain range as the electric conductivity of the sample liquid. The control calculation unit 6 selects the amplitude and optimum frequency of the AC voltage corresponding to the given electric conductivity. In the frequency corresponding to the electric conductivity of 300 µS/cm or more, "E" indicates that an error occurs, and also that, when the electric conductivity is excessively high, the measurement cannot be performed. The values listed in Table 2 are mere examples, and, actually, optimum values are set in accordance with the measuring object, the electric conductivity, and the design of the electrode.

TABLE 2

| CONDUCTIVITY OF SAMPLE LIQUID (µS/cm) | VOLTAGE (Vpp) | FREQUENCY (kHz) |
|---|---|---|
| 1– | 10 | 280 |
| 5– | 10 | 700 |
| 10– | 10 | 1000 |
| 20– | 10 | 1500 |
| 50– | 10 | 2100 |
| 100– | 10 | 3000 |
| 200– | 10 | 4400 |
| 300– | 10 | E |

Next, the optimum frequency will be described. In (Mathematical Formula 1), the dielectrophoretic force $F_{DEP}$ is proportional to the real part of the Clausius-Mossoti factor, i.e., Re[K]. As apparent from (Mathematical Formula 2) and (Mathematical Formula 3), Re[K] depends on the electric conductivity of the sample liquid 2. FIG. 7 shows how Re[K], i.e., the dielectrophoretic force changes when the electric conductivity of the sample liquid 2 is changed.

In FIG. 7, Re[K] is shown as a function of the electric conductivity of the sample liquid 2 while the electric field used in dielectrophoresis, or in other words the frequency of the applied voltage is set as a parameter. Re[K] corresponds to the dielectrophoretic force $F_{DEP}$, and the positive and negative of the force correspond to the phenomenon in which the dielectrophoretic force functions as an attractive force, and that in which the dielectrophoretic force functions as a repulsive force, respectively.

Figure 7A:
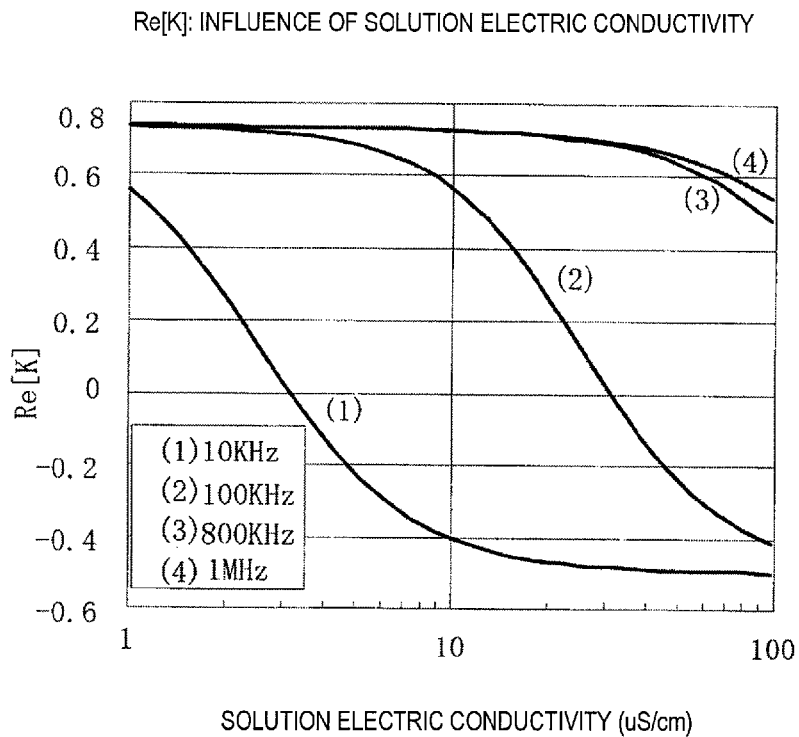
FIGS. 7(a) and 7(b) are graphs showing relationships of a solution electric conductivity (μS/cm) and Re[K] in the case where the frequency of a dielectrophoresis AC voltage is set as a parameter.

As shown in FIG. 7(a), in the case where the frequency of the dielectrophoresis AC voltage is (1) 10 kHZ, for example, Re[K] is changed from positive to negative in the vicinity of the solution electric conductivity of 3 µS/cm, and the dielectrophoretic force $F_{DEP}$ acting on the microspheres is changed from an attractive force to a repulsive force.

By contrast, in the case where the frequency of the dielectrophoresis AC voltage is (2) 100 kHZ, Re[K] is changed from positive to negative in the vicinity of the solution electric conductivity of 30 µS/cm, and the dielectrophoretic force $F_{DEP}$ acting on the microspheres is changed from an attractive force to a repulsive force.

Figure 7B:
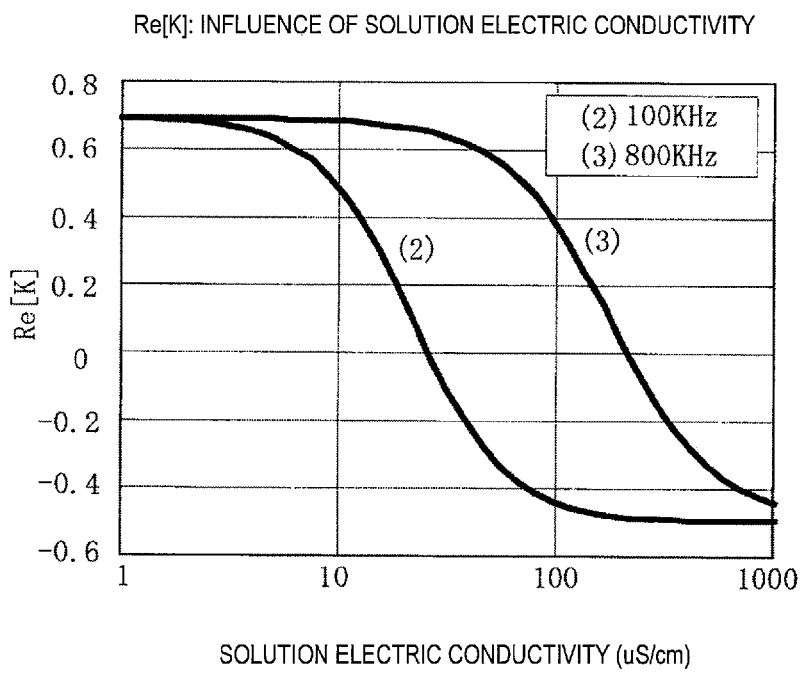

FIG. 7(b) shows changes of the dielectrophoretic force $F_{DEP}$ when the solution electric conductivity is changed from 1 µS/cm to 1,000 µS/cm in the case where the frequency of the dielectrophoresis AC voltage is (2) 100 kHz and (3) 800 kHz. In the case where the frequency is (2) 100 kHz, Re[K]<0 when about 20 µS/cm or more. However, the reduction of the dielectrophoretic force with respect to the increase of the electric conductivity is suppressed at 800 kHz, and Re[K]>0 until about 250 µS/cm, so that trapping to the edge portions in the gap 13 can be performed by an attractive force.

This shows that the optimum frequency exists at which the reduction of the dielectrophoretic force is smallest with respect to the increase of the electric conductivity of the sample liquid. The optimum frequency may be determined by performing the following experiment. Namely, a plurality of sample liquids having the same microsphere concentration and different electric conductivities are prepared, and the measurement is performed on each of the sample liquids while the frequency of the applied voltage is changed. As a result, the frequency at which the measuring response is largest is set as the optimum frequency for the sample liquid. The optimum frequencies shown in Table 2 are determined in this way.

When the frequency is excessively high, however, a measurement circuit is hardly realized, and when the frequency is excessively low, a convection flow due to Joule heat, or in an extreme case generation of bubbles due to electrolysis adversely affects the measurement. As the optimum frequency, therefore, there is a frequency in an allowable range where it is not optimum for dielectrophoresis, but can cause dielectrophoresis sufficient for performing the microsphere measurement.

Figure 8:
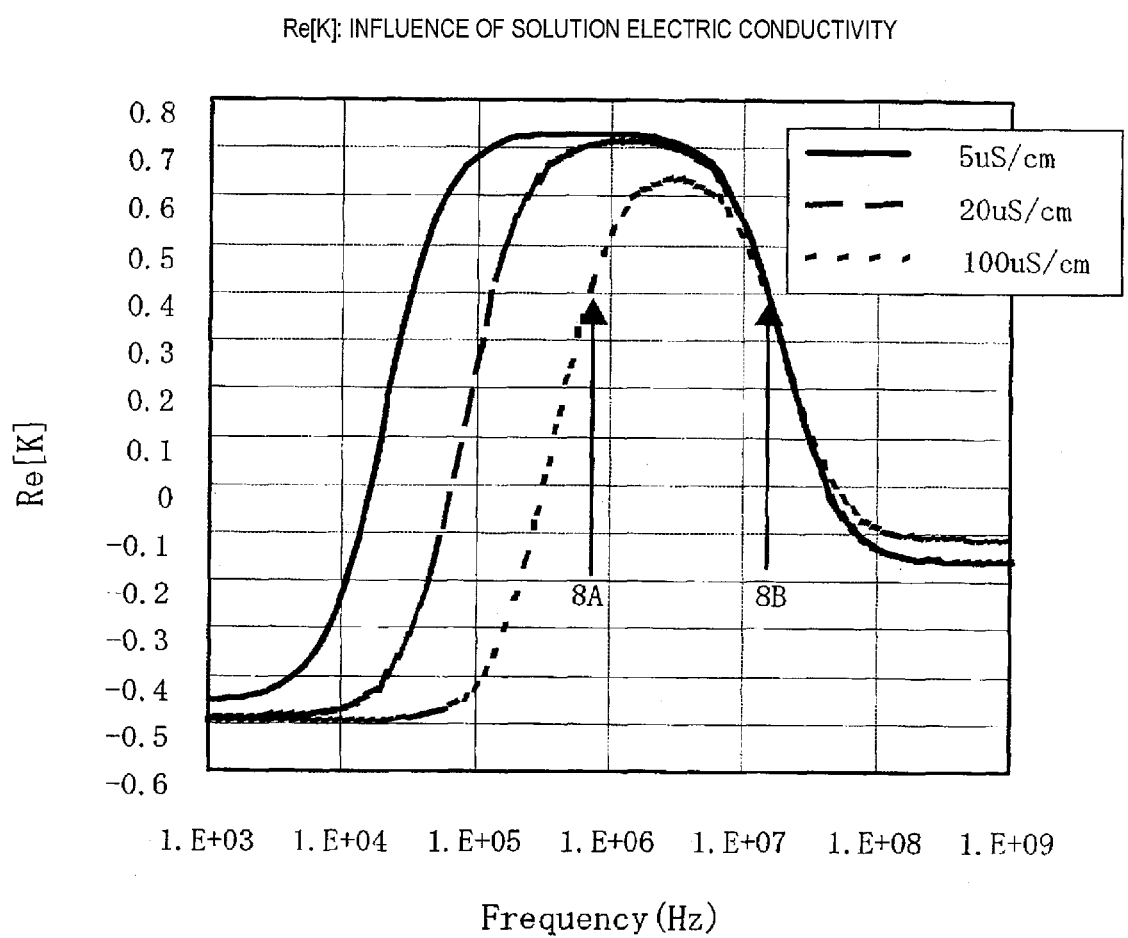
FIG. 8 is a graph showing relationships of the frequency (Hz) of the dielectrophoresis AC voltage and the real part (Re[K]) of the Clausius-Mossoti factor.

FIG. 8 is a graph showing relationships of the frequency (Hz) of the dielectrophoresis AC voltage and the real part (Re[K]) of the Clausius-Mossoti factor in the case where the solution electric conductivity (µS/cm) is set as a parameter. In the case where the microsphere measurement is performed by using positive dielectrophoresis at the sample liquid electric conductivity of 100 µS/cm, since a sufficient dielectrophoretic force by which a measuring response can be obtained is Re[K]>0.4, the optimum frequency is about 700 kHz to 4 MHz. In this case, in order to avoid the measurement circuit from being complicated because of the high frequency, 700 kHz which is the lower-limit frequency may be employed as the optimum frequency.

Furthermore, there is a case where, in the range of the sample liquid electric conductivity which must be measured, a sufficient dielectrophoretic force is obtained at one specific frequency. In this case, a frequency selection table such as shown in Table 3 is used.

TABLE 3

| CONDUCTIVITY OF SAMPLE LIQUID (μS/cm) | VOLTAGE (Vpp) | FREQUENCY (kHz) |
|---|---|---|
| 1– | 10 | 800 |
| 100– | 10 | E |

In the case where the range of the sample liquid electric conductivity which must be measured is 0 to 100 μS/cm, when the frequency is 800 kHz, for example, Re[K]>0.4 in the whole electric conductivity range, and the measurement can be performed at a single frequency in a desired sample liquid electric conductivity range. Therefore, the circuit configuration is simplified, and this is convenience. In this case, when the sample liquid electric conductivity exceeds 100 μS/cm, data corresponding to an error are written as shown in the frequency selection table.

Figure 9:
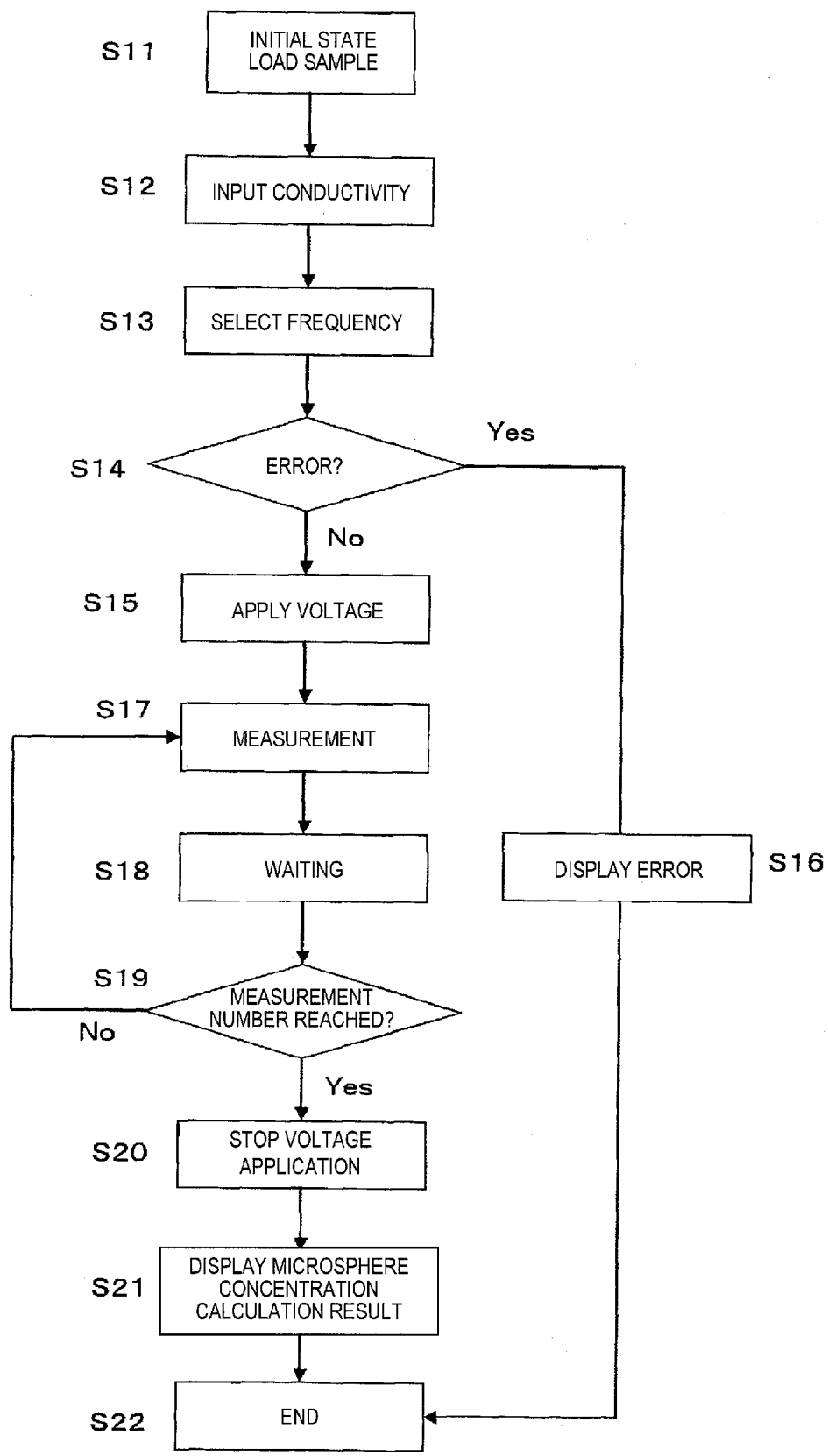
FIG. 9 is a flowchart illustrating a microsphere measuring method of the first embodiment of the invention.

FIG. 9 is a flowchart illustrating the microsphere measuring method of the embodiment. Hereinafter, a series of flows from introduction of a sample to condensation of microspheres in the cell 1, the measurement, and showing a result will be described with reference to the flowchart. First, in an initial state, a sample liquid containing microspheres which are the measuring object is loaded into the cell 1 (step S11).

Next, the electric conductivity of the loaded sample liquid is input through the conductivity inputting unit 7. The input electric conductivity is passed to the control calculation unit 6 (step S12).

The control calculation unit 6 to which the electric conductivity of the sample liquid is passed refers the optimum frequency table provided in the memory 6a, and selects the amplitude value and frequency of the voltage to be applied to the electrodes (step S13). As the voltage amplitude value (hereinafter, referred to as "voltage for dielectrophoresis") at this time, a sufficient value for trapping the microspheres to the gap 13 may be selected. In the embodiment, the voltage for dielectrophoresis is set to 10 Vp-p.

In Tables 2 and 3, the voltage for dielectrophoresis is set to a value which is constant with respect to the electric conductivity. The optimum value may be selected for each electric conductivity. In the case where the electric conductivity is high, when the voltage is excessively high, for example, Joule heat is generated, and the microsphere trap due to dielectrophoresis is affected. Therefore, for example, the voltage for dielectrophoresis is further lowered as the electric conductivity is higher.

Next, the control calculation unit 6 determines whether the frequency which is stored in the memory, and which corresponds to the input electric conductivity is an error code (E) or not (step S14). If the frequency is the error code (E), the process advances to step S16, the control calculation unit 6 instructs that the situation where the input electric conductivity is outside the measurement range is displayed on a displaying unit 9, and the measurement is ended (step S22).

If it is determined in step S14 that the selected frequency is not the error code (E), the control calculation unit 6 controls the dielectrophoresis power supply unit 4 so as to apply a voltage between the electrodes 11a, 11b at the voltage amplitude and frequency which are selected in the optimum frequency table (step S15).

When the predetermined voltage is applied between the electrodes 11a, 11b, the measurement unit 5 immediately measures the impedance between the electrodes 11a, 11b as data in the initial state immediately after the application of the voltage. The measurement result is passed to the control calculation unit 6, and stored as the initial impedance value into the memory 6a (step S17).

Here, impedance measurement is described as an example. In the case where the measurement unit 5 measures the state of the gap 13 by using optical means, the initial state can be measured even when a voltage is not applied, and hence step S17 may be performed before step S15.

Next, the control calculation unit 6 waits until a predetermined time elapses, by using time counting means which is not shown. At this time, the dielectrophoresis power supply unit 4 is maintained to hold the voltage application (step S18).

After an elapse of the predetermined time, the control calculation unit 6 determines whether a predetermined measurement number is reached or not (step S19), and, if the number is not reached, the process returns to step S17. When the process returns to step S17, the control calculation unit 6 instructs the measurement unit 5 to measure the impedance between the electrodes 11a, 11b, and a result of the measurement is stored into the memory 6a as a result after the elapse of the predetermined time.

If the predetermined measurement number is reached, the control calculation unit 6 instructs the dielectrophoresis power supply unit 4 to stop the voltage application (step S20).

After the voltage application is stopped, the control calculation unit 6 calculates the microsphere concentration in the sample liquid 2 from temporal change data of the impedance between the electrodes 11a, 11b, and stored in the memory 6a, and controls the displaying unit 9 so as to display a result (step S21), and the series of measurement operations is ended (step S22).

The calculation of the microsphere concentration can be obtained from a calibration curve which is previously stored in the memory 6a. The calibration curve uses a function showing a curve which is obtained by previously measuring a calibration sample in which the microsphere concentration is known, by using the measurement system of the microsphere measuring device that is described in the embodiment, and performing regression analysis on dispersions from correlationships of the number of microspheres at this time and the impedance change.

The conversion expression is stored into the memory 6a of the control calculation unit 6. In the case where a sample in which the microsphere concentration is not known is to be measured, when the value of an impedance change in a predetermined time is substituted, the microsphere concentration in the cell 1 can be calculated. In the case where a conversion table is used, calculation results obtained by the conversion expression are previously stored.

As described above, according to the embodiment, the optimum frequency of the applied electric field is selected in accordance with the electric conductivity of the sample liquid, so that the dielectrophoretic force which is sufficient for performing the measurement can act on microspheres. Even when the electric conductivity of the sample liquid is increased, therefore, the microspheres can be measured without performing pretreatment.

Second Embodiment

Next, a microsphere measuring device of a second embodiment of the invention will be described with reference to the drawings. The basic configuration of the microsphere measuring device of the embodiment is substantially identical with the first embodiment, and hence will be described with reference to FIGS. 5 and 2.

The microsphere measuring device of the embodiment includes: the cell 1 into which a liquid containing microspheres is to be introduced; the pair of electrodes 11a, 11b which are immersed in the cell 1; the dielectrophoresis power supply unit 4 which applies at least one of an AC voltage (hereinafter, referred to as a dielectrophoresis voltage) for inducing dielectrophoresis in microspheres, and an AC voltage (hereinafter, referred to as a measuring voltage) for measuring the impedance between the pair of electrodes 11a, 11b, between the pair of electrodes 11a, 11b; the measurement unit 5 which measures the impedance between the pair of electrodes 11a, 11b: and the control calculation unit 6 having a function of instructing the dielectrophoresis power supply unit 4 to set the frequency and amplitude of the applied voltage to have an adequate value, and that of calculating a time change of the impedance between the pair of electrodes 11a, 11b to calculate the number of the microspheres in the cell 1. As described later, it is appropriate that a relatively high frequency in the vicinity of several MHz is used as the dielectrophoresis voltage, and a relatively low frequency in the vicinity of several hundred kHz is used as the measuring voltage.

Figure 10:
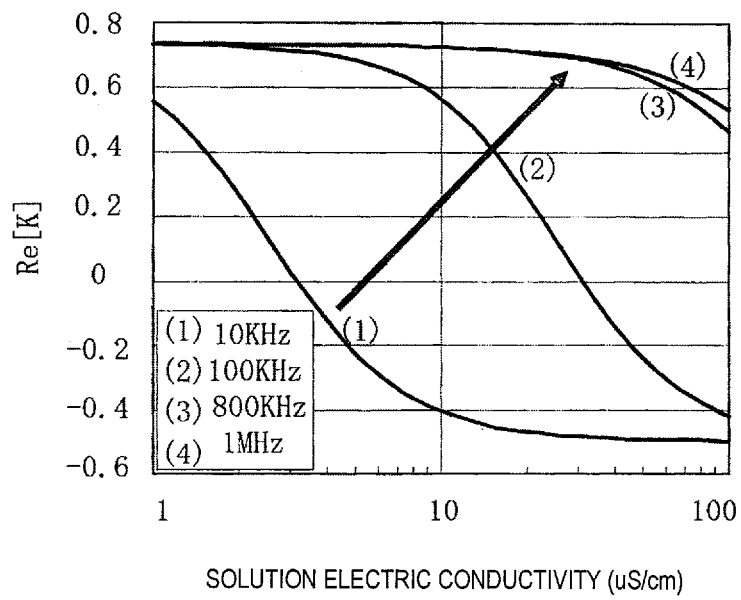
FIG. 10 is a graph showing relationships of the solution electric conductivity (μS/cm) and the real part (Re[K]) of the Clausius-Mossoti factor in the case where the frequency of the dielectrophoresis AC voltage is set as a parameter.

FIG. 10 is a graph showing relationships of the solution electric conductivity (μS/cm) and the real part (Re[K]) of the Clausius-Mossoti factor in the case where the frequency of the dielectrophoresis voltage is set as a parameter. Re[K] corresponds to the dielectrophoretic force $F_{DEP}$, and the positive and negative of Re[K] correspond to the phenomenon in which the dielectrophoretic force functions as an attractive force, and that in which the dielectrophoretic force functions as a repulsive force, respectively.

As shown in the figure, in the case where the frequency of the dielectrophoresis voltage is (1) 10 kHZ, for example, Re[K] is changed from positive to negative in the vicinity of the solution electric conductivity of 3 μS/cm, and the dielectrophoretic force $F_{DEP}$ acting on the microspheres is changed from an attractive force to a repulsive force.

By contrast, in the case where the frequency of the dielectrophoresis voltage is (2) 100 kHZ, Re[K] is changed from positive to negative in the vicinity of the solution electric conductivity of 30 μS/cm, and the dielectrophoretic force $F_{DEP}$ acting on the microspheres is changed from an attractive force to a repulsive force.

When the frequency of the dielectrophoresis voltage is further raised to (3) 800 kHz or (4) 1 MHz, the positive dielectrophoretic force $F_{DEP}$ acting on the microspheres is maintained even in the case where the solution electric conductivity is increased. Therefore, the influence of the solution electric conductivity is smaller as the frequency of the dielectrophoresis voltage is higher, and it is known that a higher frequency of the dielectrophoresis voltage is advantageous to efficient trapping of microspheres.

Figure 12:
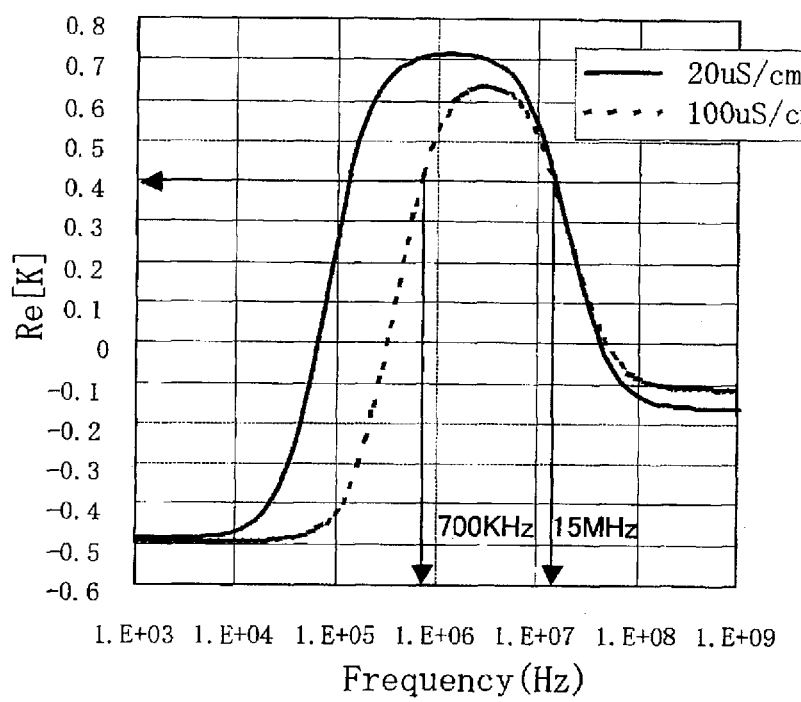
FIG. 12 is a graph showing relationships of the frequency (Hz) of the dielectrophoresis voltage and Re[K] in the case where the solution electric conductivity (μS/cm) is set as a parameter.

FIG. 12 is a graph showing relationships of the frequency (Hz) of the dielectrophoresis voltage and Re[K] in the case where the solution electric conductivity (μS/cm) is set as a parameter. In this case, there is a high possibility that the electric conductivity of the sample liquid is 20 μS/cm or higher. In the case where the electric conductivity of the sample liquid is 20 μS/cm, when the frequency of the dielectrophoresis voltage is about 50 kHz or higher, the dielectrophoretic force $F_{DEP}$ is changed from a repulsive force to an attractive force. Therefore, the frequency of the dielectrophoresis voltage is required to be at least 50 kHz or higher. By contrast, when the frequency of the dielectrophoresis voltage is excessively high, Re[K] is lowered irrespective of the solution electric conductivity, and, at 50 MHz, the dielectrophoretic force $F_{DEP}$ is changed from an attractive force to a repulsive force. Therefore, it is preferable that the frequency of the dielectrophoresis voltage is between 50 kHz and 50 MHz.

In some cases, it is assumed that the electric conductivity of a sample liquid is 100 μS/cm or higher. In order to enable also the sample liquid to be measured, therefore, the range of 700 kHz to 15 MHz is most preferable because Re[K] is 0.5 or more and hence a sufficient dielectrophoretic force can be induced in microspheres.

In the embodiment, it is requested that the frequency of the dielectrophoresis voltage is set to 3 MHz, a value which is sufficient for trapping microspheres in the gap 13 is selected as the amplitude, and 10 Vp-p is set.

Figure 11:
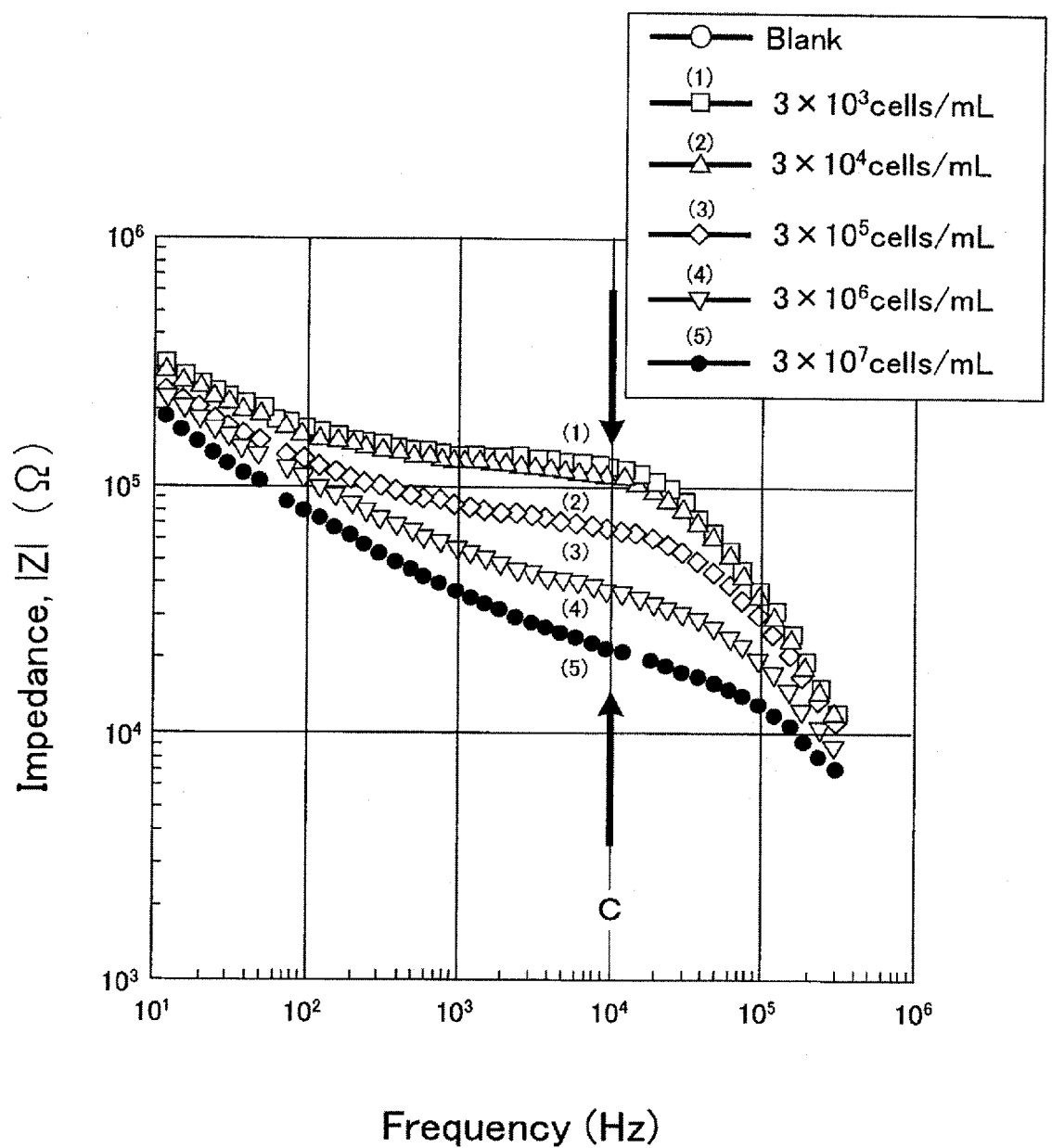
FIG. 11 is a graph showing relationships of the frequency of an AC voltage for measuring an impedance and the impedance of a solution in the case where the number of microspheres in the solution is set as a parameter.

On the other hand, FIG. 11 is a graph showing relationships of the frequency of the measuring voltage and the impedance of a solution in the case where the number of microspheres in the solution is set as a parameter. As shown in the figure, with respect to numbers of microspheres of (1) $3 \times 10^3$ cells/mL to (5) $3 \times 10^7$ cells/mL, the changing width of the absolute value |Z| of the impedance is maximum (about 20 KΩ to 150 KΩ) in the vicinity of 10 kHz (the arrow C) of the frequency the measuring voltage. Therefore, it can be said that a frequency in the vicinity of 10 kHz is most optimum for the impedance measurement.

As the frequency is higher, usually, it is more difficult to maintain the accuracy of the impedance measurement. When the impedance measurement is to be performed in a region of a relatively high frequency of about 1 to 10 MHz which is optimum as the frequency of the dielectrophoresis voltage, the measurement circuit is complicated, and it is difficult to realize a highly accurate impedance measurement circuit. Therefore, the impedance measurement is performed while setting the frequency of the measuring voltage to a relatively low-frequency region of about 10 kHz to 1 MHz. In the embodiment, different frequencies can be individually selected in dielectrophoresis and an impedance measurement, and hence there is an effect that conditions which are optimum respectively for dielectrophoresis and an impedance measurement, and also a highly accurate impedance measurement can be realized by a simple measurement circuit.

When the solution electric conductivity is about 3 μS/cm or higher, the vicinity of the frequency of 10 kHz which is most suitable in the measuring voltage is in the negative dielectrophoresis region, and impedes dielectrophoresis due to the dielectrophoresis voltage. Therefore, such a frequency is not suitable for trapping microspheres between the electrodes 11a, 11b. Consequently, it is preferable that the frequency is made higher to the extent permitted by the impedance measurement accuracy, and the amplitude is made smaller as compared with the dielectrophoresis voltage. Most preferably, the frequency of the measuring voltage is a frequency at which negative dielectrophoresis does not occur at the electric conductivity of the measurement sample liquid.

Figure 13:
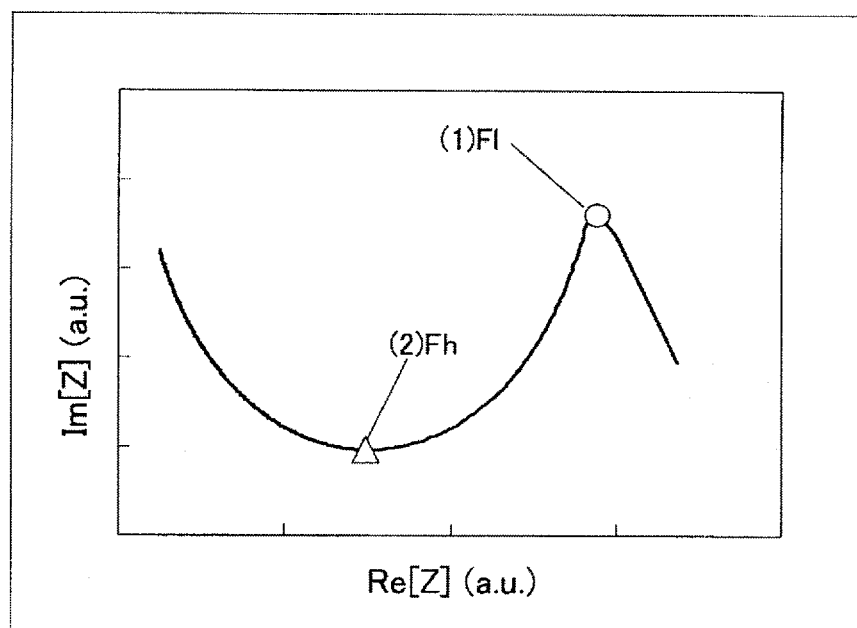
FIG. 13 is a view showing relationships of the real part (abscissa) and imaginary part (ordinate) of an electrode impedance in the case where the measurement is performed while sweeping the frequency in an example of the invention.

In the selection of the frequency which is optimum for an impedance measurement, furthermore, there is a problem in that, when the impedance measurement is performed in a frequency region where an influence of the Warburg impedance caused by an influence of diffusion in the interfaces between the electrodes and the sample liquid occurs, a correct impedance cannot be measured. FIG. 13 is a view (referred to as a Cole-Cole plot) showing relationships of the real part (abscissa) and imaginary part (ordinate) of an electrode impedance in the case where the measurement is performed while sweeping the frequency.

Referring to FIG. 13, the high-frequency side with respect to the boundary at the frequency (referred to as F1) in (1)

forms a semicircular locus (the left side from (1)), and an equivalent circuit of the electrode system is described by a simple model configured by parallel connection of a resistor and a capacitor. On the other hand, the low-frequency side (the right side from (1)) with respect to Fl is a region where an influence of the Warburg impedance occurs and the Cole-Cole plot is deviated from the semicircle. In the invention, the frequency of Fl is called the boundary frequency. Unlike a simple equivalent circuit model configured by a parallel circuit of a resistor and a capacitance, the diffusion coefficient of a material related to electron transfer between the electrodes and the solution, and the like are complicated. With respect to the impedance in the region where the plot is deviated from the semicircle, therefore, the impedance change due to trapping of microspheres to the electrodes cannot be correctly calculated. In order to perform a measurement by the DEPIM method, consequently, the impedance must be measured in a frequency region of Fl or higher where an influence of the Warburg impedance does not occur. In order to determine the frequency of the measuring voltage, the Cole-Cole plot is measured by using an actual electrode system and a solution (not containing microspheres) having an assumed electric conductivity.

From the viewpoint of an impedance measurement circuit, in order to prevent a measurement error due to a flow of an unwanted current from occurring, preferably, the level of the impedance at the frequency of the measuring voltage is as high as possible. Therefore, it is preferable to select a frequency in a range extending to the apex (the point of (2) in FIG. 13, referred to as Fh) of the semicircle of the Cole-Cole plot.

A frequency which is equal to or higher than Fl and equal to or lower than Fh, Fl and Fh being obtained from measurement results, and at which a desired measurement accuracy can be ensured may be determined as the frequency of the measuring voltage. In the embodiment, the frequency of the measuring voltage is set to 800 kHz.

In the embodiment, the measuring object is microspheres contained in blood or saliva, specifically a bacterium is measured. In blood or saliva, the electric conductivity is varied depending on the measuring object or a human or an animal, or the specimen collection time. In industrial materials, the electric conductivities of liquids which are introduced into two cells can be matched with each other. Therefore, a configuration in which, in order to detect only an impedance change due to trapping of a bacterium in electrodes, a solution containing the bacterium that is a measuring object is introduced into one cell, that having the same electric conductivity as the solution of the measuring object, and not containing the bacterium of the measuring object is introduced into another cell, and impedance change components other than those due to trapping of the bacterium are cancelled is seemed to be effective. In a measurement of blood or saliva of a human or an animal, however, the two-cell type cannot be used because of the following reason. As described above, the electric conductivity of a specimen is largely changed depending on the subject or the collection time, and hence it is extremely difficult and in some cases impossible to prepare solutions of the same electric conductivity for every specimen. Considering this, and supposing that, even when specimens are collected from different humans or animals or at different collection times, the inventors intensively studied. As a result, when a measurement is performed as described above at a frequency that is higher than that at which an influence of the Warburg impedance occurs, a stable measurement is enabled. In the above-described example, with respect to the frequency that is higher than that at which an influence of the Warburg impedance occurs, the frequency which is affected by the Warburg impedance has a value which is lower than 100 kHz. Therefore, it is contemplated that a signal of a frequency which is higher than this may be applied. In a human or an animal, as described above, however, the electric conductivity is largely varied depending on a human or an animal, or the specimen collection time. Considering these, in the embodiment, a measurement voltage of a frequency range from 800 kHz to a frequency which is lower than a frequency for dielectrophoresis is applied. In the embodiment, among them, the detection can be sufficiently provided with stability at 800 kHz, and therefore the measurement can be performed at a frequency which is slightly higher than 800 kHz. It is a matter of course that the measurement may be performed at a higher frequency. However, such a frequency cannot be separated from 3 MHz which is the frequency for dielectrophoresis in the embodiment, and hence a realistic frequency is about 2 MHz at the highest.

Figure 14:
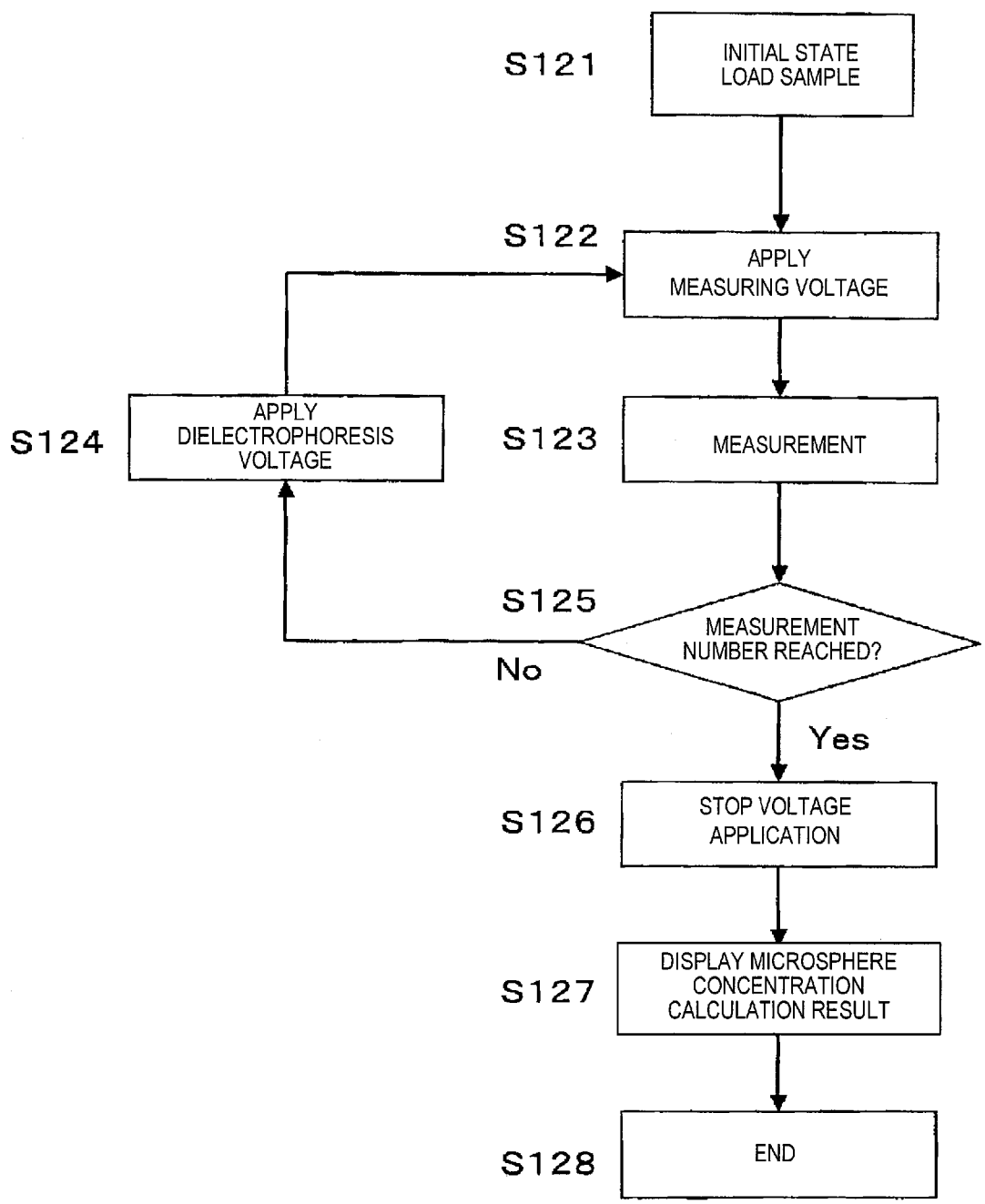
FIG. 14 is a flowchart illustrating a microsphere measuring method of a second embodiment of the invention.

FIG. 14 is a flowchart illustrating a microsphere measuring method of the embodiment. Hereinafter, a series of flows from introduction of a sample to concentration of the microspheres in the cell 1, measurement, and presentation of a result will be described with reference to the flowchart.

First, in an initial state, the sample liquid containing microspheres which are the measuring object is loaded into the cell 1 (step S121). The control calculation unit 6 which detects the introduction of the sample liquid by means of a user's operation or a liquid sensing unit which is not shown instructs the dielectrophoresis power supply unit 4 to apply the frequency and amplitude of the measuring voltage that is previously stored in the memory 6a, and the dielectrophoresis power supply unit 4 applies the instructed measuring voltage between the electrodes 11a, 11b (step S122).

When the measuring voltage is applied, the measurement unit 5 immediately measures, in accordance with the instructions of the control calculation unit 6, the current between the electrodes 11a, 11b. The measurement result is transferred to the control calculation unit 6, and the impedance is calculated and stored in the memory 6a (step S123).

When the impedance measurement is ended, the control calculation unit 6 determines whether a measurement number (or measurement time) which is previously stored in the memory 6a is satisfied or not (step S125). If not satisfied, the control calculation unit 6 instructs the dielectrophoresis power supply unit 4 to apply the dielectrophoresis voltage of the frequency and amplitude that are previously stored in the memory 6a, and the dielectrophoresis power supply unit 4 applies the instructed dielectrophoresis voltage between the electrodes 11a, 11b (step S124).

When a predetermined time elapses, the control calculation unit 6 instructs the dielectrophoresis power supply unit 4 to change the applied voltage to the measuring voltage, and the dielectrophoresis power supply unit 4 changes the voltage applied between the electrodes 11a, 11b, from the dielectrophoresis voltage to the measuring voltage (step S122). At this time, microspheres are trapped between the electrodes 11a, 11b by the application of the dielectrophoresis voltage, but, after changed to the measuring voltage, the dielectrophoresis voltage is not applied. The measuring voltage preferably has a relatively low frequency of about several hundred kHz. In the state where the electric conductivity is high, therefore, this can be said to be conditions under which positive dielectrophoresis is hardly induced. When the time of application of the measuring voltage is long, therefore, there is a possibility that the microspheres which are once trapped by the dielectrophoresis voltage are dispersed from the gap between the electrodes 11a, 11b by an external force such as the viscous force of the sample liquid or gravity sedimentation. Therefore, the measuring voltage is preferably applied for a time which is within the time when the measurement unit 5 can measure a current with necessary and sufficient accuracy, which is shorter than at least the application time of the dielectrophoresis voltage, and which is as short as possible, and most preferably applied for about 10 ms to 100 ms. According to the configuration, there is an effect that the microspheres trapped by the dielectrophoresis voltage during application of the measuring voltage are held without being dispersed from the electrodes during application of the measuring voltage, whereby a highly sensitive impedance measurement can be realized.

Hereinafter, similar steps are repeated. If the predetermined measurement number (or measurement time) is satisfied in step S125, the process proceeds to step S126 for ending the measurement. The control calculation unit 6 instructs the dielectrophoresis power supply unit 4 to stop the voltage application, and the dielectrophoresis power supply unit 4 stops the voltage application. In step S127, then, the control calculation unit 6 calculates the concentration of the microspheres, and displays a result, thereby completing the measurement operations. The details of the operations are identical with those of the above-described embodiment, and therefore their description is omitted.

In the microsphere measuring device of the embodiment, as described above, microspheres are trapped at a high frequency at which the influence of the solution electric conductivity is small, and which is advantageous to dielectrophoresis, and the impedance measurement is performed by a low frequency at which the changing width of the absolute value |Z| of the impedance is broad, or in other words the impedance measurement is facilitated and has a high sensitivity. Therefore, both a dielectrophoretic trap under conditions of a high solution electric conductivity, and a highly sensitive and accurate impedance measurement can be attained.

The embodiment has been described with the assumption that the amount to be measured is an impedance. As the amount to be measured, alternatively, the current flowing through the electrodes, the phase difference between the voltage and the current, the dielectric constant, the electric conductivity, or an electrophysical characteristic value which is calculated from these may be used. In the embodiment, among these, the impedance, and the resistance component (conductance) and capacitance component (capacitance) of the impedance are measured to measure microspheres.

In the microsphere measuring device of the embodiment, the control calculation unit 6 may select the frequency of the dielectrophoresis voltage and that of the measuring voltage, based on the solution electric conductivity. As described above, the dielectrophoretic force is changed depending on the solution electric conductivity, and the frequency which is optimum for the impedance measurement may be different in accordance with the electric conductivity. With respect to the frequencies of the dielectrophoresis voltage and the measuring voltage, therefore, it is necessary to respectively select optimum values in accordance with the solution electric conductivity.

Here, the solution electric conductivity can be obtained from the measurement result of the impedance between the electrodes 11a, 11b, because the conductance which is the reciprocal of the resistance component of the impedance has a value reflecting the solution electric conductivity. In advance of the measurement, therefore, the impedance of the sample liquid is measured to obtain the electric conductivity, and optimum frequencies of the dielectrophoresis and measuring voltages are selected.

According to the configuration, even in a sample liquid in which the electric conductivity is changed, it is possible to realize both a trap of microspheres due to sure dielectrophoresis, and a highly accurate impedance measurement.

Third Embodiment

In the second embodiment, the microsphere measuring device in which the dielectrophoresis power supply unit 4 sequentially applies the dielectrophoresis voltage and the measuring voltage has been described. In the embodiment, the case where, in the microsphere measuring device described in the second embodiment, the dielectrophoresis power supply unit 4 simultaneously applies the dielectrophoresis voltage and the measuring voltage will be described. In the microsphere measuring device (not shown) of the embodiment, the measurement unit 5 in the configuration of FIG. 5 has a filter separation function which will be described later.

In the embodiment, the dielectrophoresis power supply unit 4 applies in a superimposed manner an AC voltage of a high frequency in the vicinity of 1 MHz as the dielectrophoresis voltage, and an AC voltage of a low frequency in the vicinity of 10 kHz to 1 MHz as the measuring voltage, between the electrodes 11a, 11b. The reason of the condition setting is identical with that of the second embodiment. Furthermore, the measurement unit 5 can filter-separate frequency components of the AC voltage of the low frequency in the vicinity of 10 kHz to 1 MHz, and measure the impedance between the electrodes 11a, 11b.

The superimposition in this context means addition of AC signals of at least two different frequencies such as a sinusoidal wave or a rectangular wave, to produce an AC signal. The filter separation function is a function of taking out only specific frequency components from the AC signal. The filter separation function is realized by a known technique such as a passive filter configured by an RC circuit and consisting of passive elements, an active filter configured by active elements such as an operation amplifier, or a digital filter due to signal processing. In the embodiment, the signal of the low-frequency measuring voltage must be separated from the signal in which the high-frequency dielectrophoresis voltage is mixed, and hence the filter is configured as a low-pass filter.

Furthermore, the signal of the measuring voltage of a low amplitude must be separated from that of the dielectrophoresis voltage of a high amplitude. Therefore, only the frequency components of the measuring voltage are taken out by a phase detection system which can take out a low-level signal of a specific frequency from a signal containing high-noise components, thereby realizing a highly accurate impedance measurement.

According to the configuration, AC voltages of a high frequency of 1 MHz or higher and a low frequency in the vicinity of 10 kHz are applied in a superimposed manner, the frequency components of the AC voltage of the low frequency in the vicinity of 10 kHz are filter-separated, and then the impedance is measured. Therefore, the trapping of microspheres and the impedance measurement can be simultaneously performed, the state where only the measurement voltage is applied does not occur, and the impedance can be measured while microspheres remain to be firmly trapped between the electrodes, with the result that microsphere detection which is highly accurate and sensitive can be realized. Namely, the trapping is performed at the high frequency, and the measurement is performed at the low frequency, so that both avoidance of the influence of the electric conductivity, and a highly accurate impedance measurement can be achieved. Since the measurement is performed at the low frequency, furthermore, the measurement circuit can be configured by a simple circuit which is advantageous in design, and the cost of which is low. Moreover, the use of the superimposed wave of the high frequency and the low frequency enables the measurement and the trapping to be simultaneously performed.

In the microsphere measuring device of the embodiment, the control calculation unit 6 may adjust one of the frequencies of the voltages which are applied based on the solution electric conductivity, namely, the frequencies of the dielectrophoresis voltage and the measurement voltage.

When the frequencies of the dielectrophoresis voltage and the measurement voltage are set to adequate values in accordance with the electric conductivity of the sample liquid as described above, respectively, there is an effect that the trapping of microspheres and the impedance measurement can be performed more surely and highly accurately.

Hereinafter, an example of Embodiment 3 will be shown.

Figure 15:
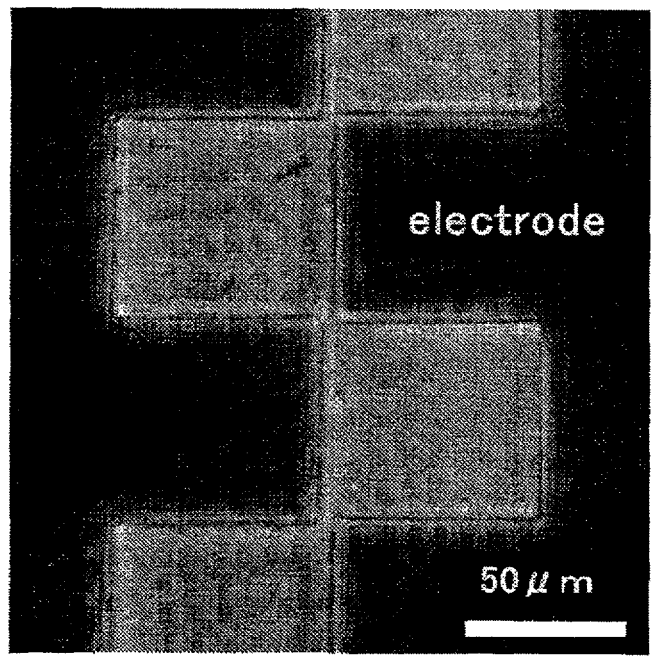
FIG. 15 is a view showing electrodes in an example of the invention.

EXAMPLE (1) Setting of Frequency of Dielectrophoresis Voltage and Amplitude of Measurement Voltage Experiments for studying optimum values of the frequencies and amplitudes of the dielectrophoresis voltage and the measuring voltage were conducted. A material obtained by harvesting *Escherichia coli* K-12 strain (NBRC 3301, Institute of Technology and Evaluation) in which aerobic cultivation was performed at 37° C. and for 16 hours on a standard agar medium (MB0010, EIKEN KIZAI K.K.), by a bacteria spreader, and suspending the harvested strain and adequately diluting in 0.1 M D-mannitol solution (the electric conductivity, about 5 µS/cm) was set as a sample. An NaCl solution was adequately added to the sample to prepare the sample liquid electric conductivity. The sample liquid electric conductivity was measured by an electric conductivity meter (B-173, Horiba, Ltd.). In order to observe the manner in which microorganisms are dielectrophoresed, as the electrodes, electrodes in which rectangles shown in FIG. 15 are nested were used. The electrodes were covered by a transparent chamber, and observed under phase-contrast microscope (IX70, Olympus).

Figure 16A:
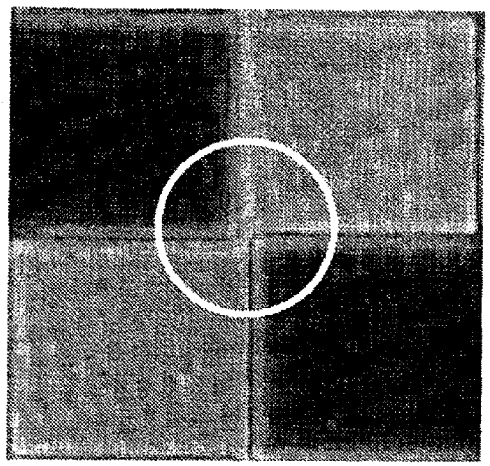
FIGS. 16(a) to 16(c) are views which show the state of an electrode gap after 40 seconds from a voltage application in the example of the invention, and in which the frequency of a dielectrophoresis voltage is 100 kHz in FIG. 16(a), 800 kHz in FIG. 16(b), and 3 MHz in FIG. 16(c).
Figure 16B:
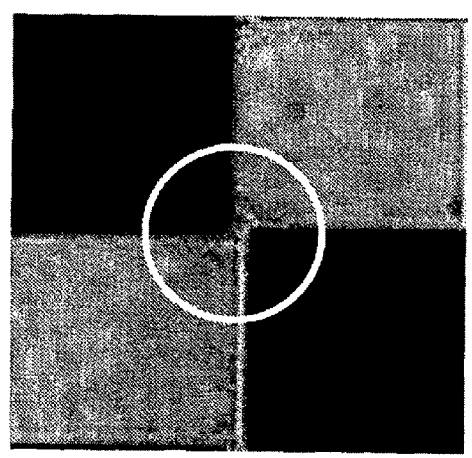
Figure 16C:
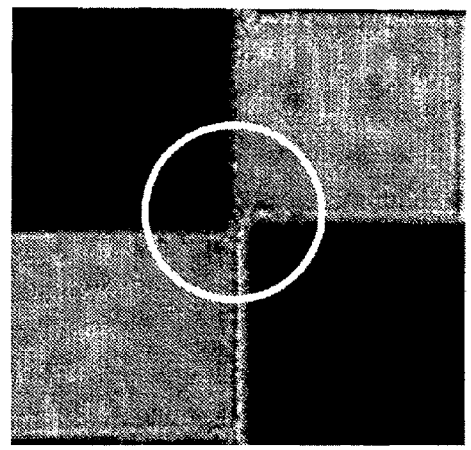

FIG. 16 shows the state of an electrode gap after 40 seconds from the voltage application, and in which the frequency of the dielectrophoresis voltage is 100 kHz in FIG. 16(*a*), 800 kHz in FIG. 16(*b*), and 3 MHz in FIG. 16(*c*). The electric conductivity of the sample liquid is 100 µS/cm. The applied voltage is 10 Vp-p, and the AC voltage is a sinusoidal wave. In the cases of FIGS. 16(*b*) and 16(*c*) where the frequency is high, it is seen that *Escherichia coli* is trapped to a high electric field region in the electrode gap (corner portions of the electrodes, in the white circle). By contrast, in the case of FIG. 16(*a*) where the frequency is low, *Escherichia coli* is little trapped to the electrodes, and it was known that, in the case where the electric conductivity of the sample liquid is 100 µS/cm, it is impossible to trap microorganisms to the electrodes at 100 kHz.

Figure 17A:
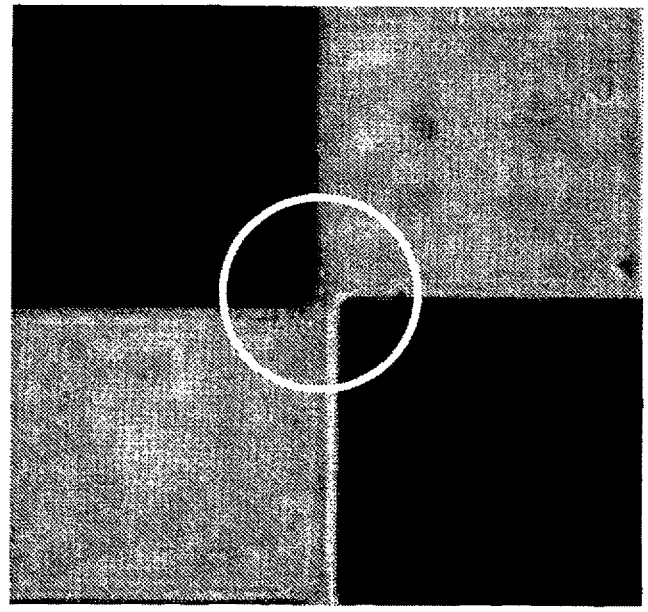
FIGS. 17(a) and 17(b) are views which show the state of the electrode gap in the example of the invention in the case where the sample liquid electric conductivity is 300 μS/cm, and in which the frequency of the dielectrophoresis voltage is 800 kHz in FIG. 17(a), and 3 MHz in FIG. 17(b).
Figure 17B:
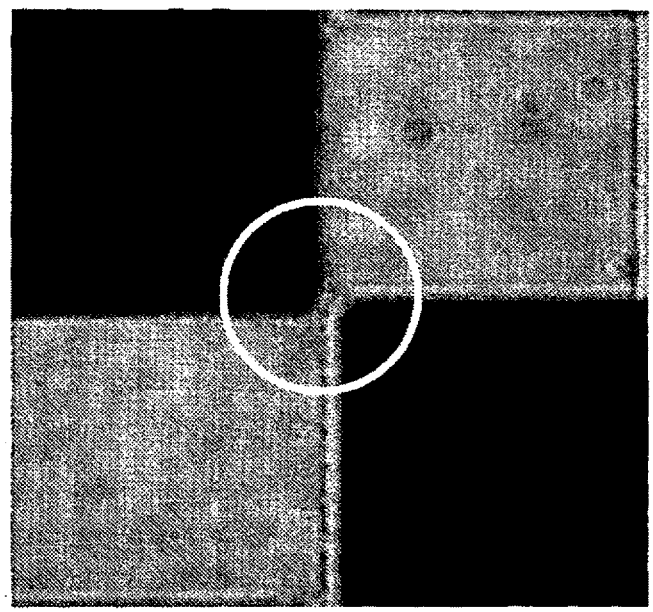

FIG. 17 shows the state of the electrode gap in the case where the sample liquid electric conductivity is 300 µS/cm, and in which the frequency of the dielectrophoresis voltage is 800 kHz in FIG. 17(*a*), and 3 MHz in FIG. 17(*b*). It was confirmed that, at the frequency of 3 MHz, as compared with 800 kHz, a larger number of *Escherichia coli* are trapped, and, when the electric conductivity is raised, 3 MHz is the most suitable conditions.

Figure 18A:
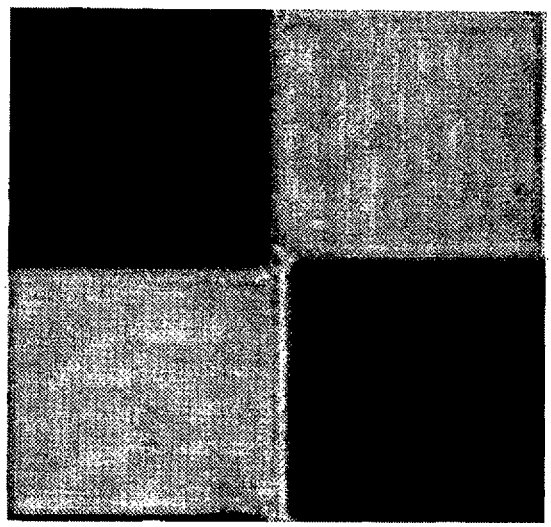
FIGS. 18(a) and 18(b) are views showing states of electrode gaps in the example of the invention in the case where 3 MHz, 10 Vp-p is applied as the frequency of the dielectrophoresis voltage, and 100 kHz is superimposedly applied as the frequency of the measurement voltage.
Figure 18B:
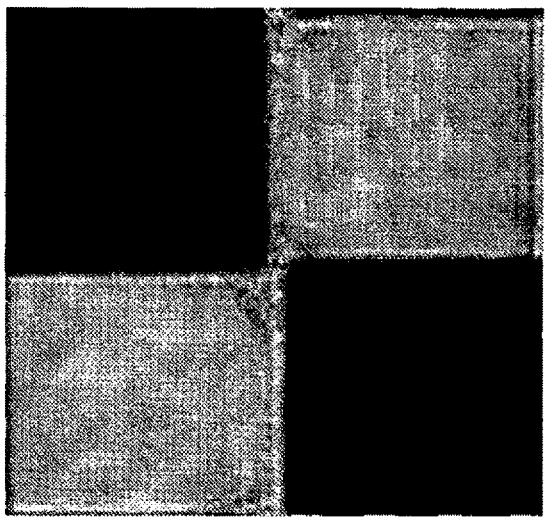

FIG. 18 shows the states of electrode gaps in the case where 3 MHz, 10 Vp-p is applied as the frequency of the dielectrophoresis voltage, and 100 kHz is superimposedly applied as the frequency of the measurement voltage. The electric conductivity of the sample liquid is 200 µS/cm. In the figure, FIG. 18(*a*) shows the case where the amplitude of 100 kHz (the frequency of the measuring voltage) is 3 Vp-p, and FIG. 18(*b*) shows the case where the amplitude of 100 kHz is 1 Vp-p. It is known that, in the case where the amplitude of the measuring voltage of the low frequency is high or 3 Vp-p, as compared with the case of 1 Vp-p, the amount of trapped *Escherichia coli* is small due to negative dielectrophoresis effect caused by 100 kHz voltage. Therefore, it was confirmed that the optimum amplitude of the measuring voltage is about 1 Vp-p.

Figure 20:
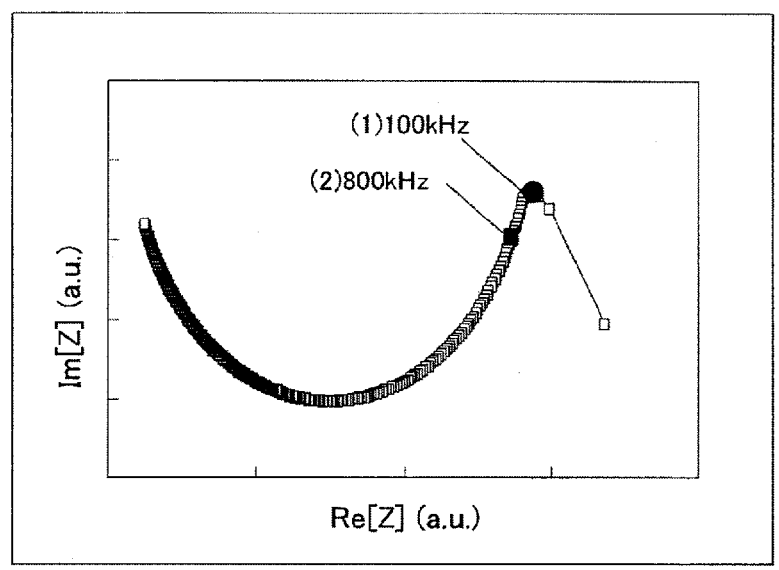
FIG. 20 is a Cole-Cole plot of the electrode impedance in the example of the invention in the case where the electric conductivity of the solution is 240 μS/cm.
Figure 21A:
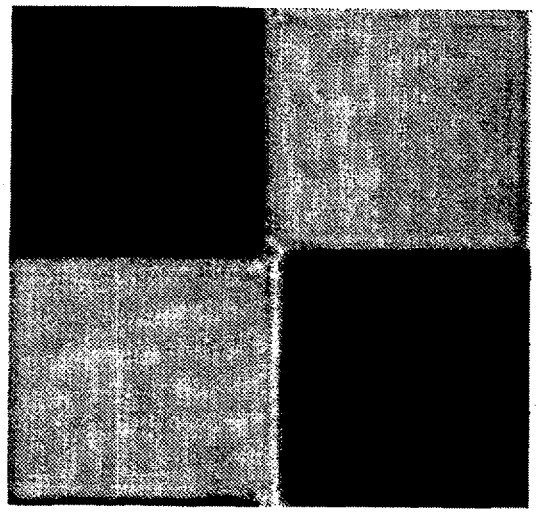
FIGS. 21(a) and 21(b) are views which show the states of electrode gaps in the example of the invention in the case where 100 kHz in FIG. 21(a) and 800 kHz in FIG. 21(b) are superimposedly applied as the frequency of the measurement voltage.
Figure 21B:
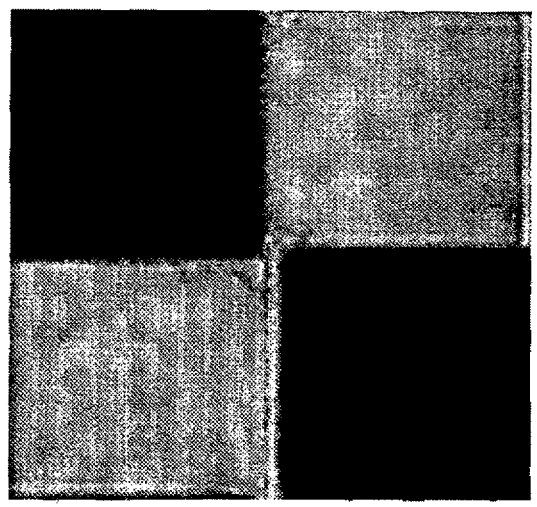

FIG. 20 is a Cole-Cole plot of the electrode impedance in the case where the electric conductivity of the solution is 240 µS/cm. From the figure, it is known that Fl=100 kHz. Therefore, the frequency of the measuring voltage must be 100 kHz or higher. FIG. 21 shows the states of electrode gaps in the case where 3 MHz, 10 Vp-p is applied as the frequency of the dielectrophoresis voltage, and 100 kHz in FIG. 21(*a*) and 800 kHz in FIG. 21(*b*) are superimposedly applied as the frequency of the measurement voltage. The electric conductivity of the sample liquid is 200 µS/cm. It is known that, at the high frequency or 800 kHz, the amount of trapped *Escherichia coli* is large as compared with the case of the frequency of the measuring voltage is low or 100 kHz because no negative dielectrophoresis effect occurs at 800 kHz frequency. Therefore, it was confirmed that the optimum frequency of the measuring voltage is about 800 kHz.

(2) Measurement of Microorganisms

Figure 19A:
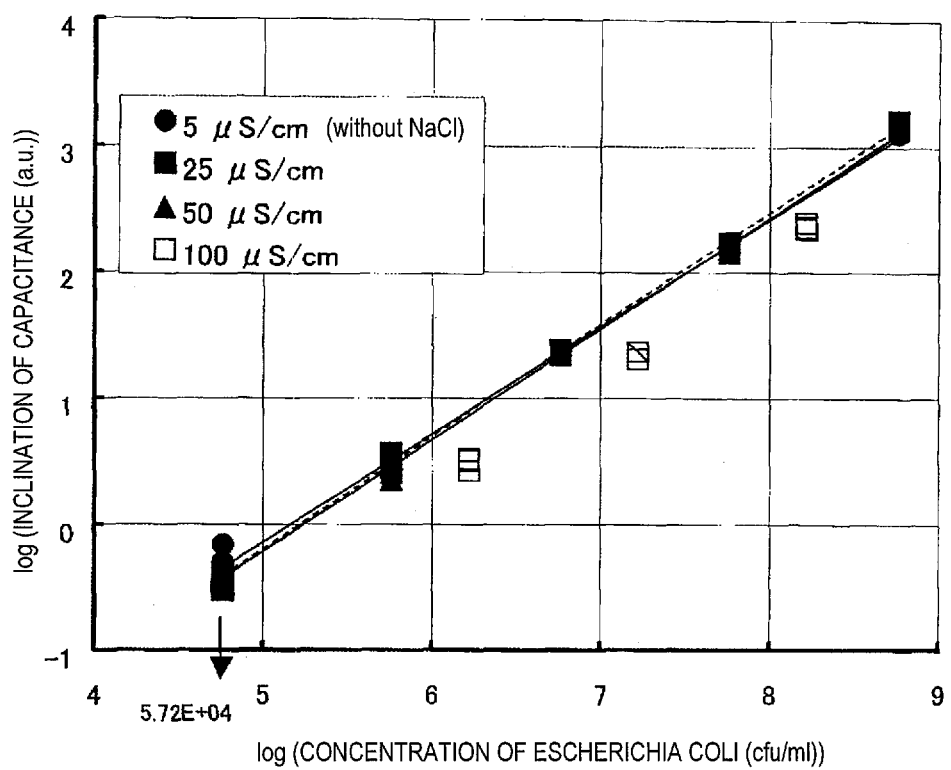
FIGS. 19(a) and 19(b) are views showing a logarithmic graph of the concentration of *Escherichia coli* and a response value (inclination of a capacitance) of a DEPIM measurement in the example of the invention.
Figure 19B:
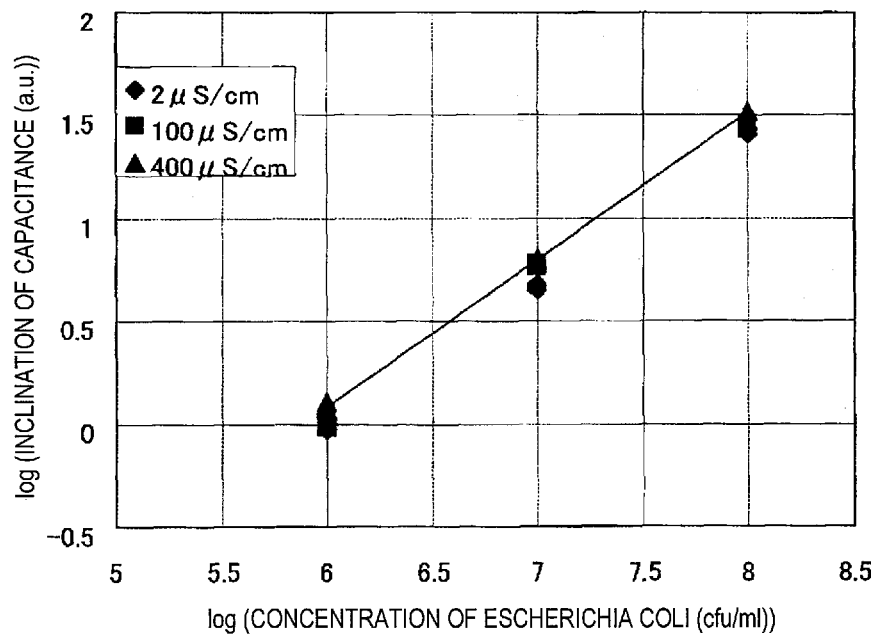

From the above-described experiments, the dielectrophoresis voltage was defined as 3 MHz, 10 Vp-p, and the measurement voltage was defined as 800 kHz, 1 Vp-p. Sample liquids in which the concentration of *Escherichia coli* and the electric conductivity are adequately adjusted were subjected to measurement by the device of FIG. 5. For comparison, similar measurements were performed while the dielectrophoresis voltage and the measurement voltage are set identically or to 800 kHz, 10 Vp-p. FIG. 19 shows logarithmic graphs in which the abscissa indicates the concentration of *Escherichia coli*, and the ordinate indicates the response value (inclination of the capacitance) of the DEPIM measurement. In the graph, FIG. 19(*a*) shows the case where both the dielectrophoresis voltage and the measuring voltage are set to 800 kHz, and FIG. 19(*b*) the case where the dielectrophoresis voltage is set to 3 MHz and the measuring voltage is set to 800 kHz. In the case of FIG. 19(*a*), when the sample liquid electric conductivity is raised to 100 µS/cm, the dielectrophoretic force acting on the microorganisms is reduced, with the result that also the response value of the DEPIM measurement is observed to be reduced. By contrast, in the case where the dielectrophoresis voltage and the measuring voltage are adequately set, even when the sample liquid electric conductivity is raised to 400 µS/cm, as shown in FIG. 19(*b*), a response reduction is not observed, and it was shown that a highly accurate measurement is enabled.

Although the invention has been described in detail and with reference to the specific embodiments, it is obvious to those skilled in the art that various changes and modifications can be made without departing from the spirit and scope of the invention.

The application is based on Japanese Patent Application (No. 2009-028927) filed Feb. 10, 2009, the contents of which are incorporated herein by reference.

INDUSTRIAL APPLICABILITY

The invention is useful as a microsphere measuring device and microsphere measuring method in which both a dielectrophoretic trap at a high solution electric conductivity, and a highly sensitive and accurate impedance measurement can be attained.

DESCRIPTION OF REFERENCE SIGNS 1 cell
2 sample liquid
3 electrode chip
4 dielectrophoresis power supply unit measurement unit
6 control calculation unit
6a memory
7 conductivity inputting unit
9 displaying unit
10 substrate
11a, 11b electrode
13 gap
14 microsphere
15 electric force line
17 stirring unit
21 light source
22 light receiving portion

The invention claimed is:

1. A method for measuring microspheres in a liquid sample comprising at least one of blood and saliva, comprising:
   a step of applying an AC voltage having a first frequency between the pair of electrodes to cause a dielectrophoretic force to act on the microspheres;
   a step of applying an AC voltage having a second frequency between the pair of electrodes to measure an impedance between the pair of electrodes, the second frequency being higher than a frequency at which an influence of a Warburg impedance occurs, wherein the applying the AC voltage having the first frequency is terminated and then the AC voltage having the second frequency is applied;
   a step of measuring the impedance between the pair of electrodes; and
   a step of calculating a time change of the impedance between the pair of electrodes, and calculating a number of the microspheres in the cell,
   wherein a time period for applying the AC voltage having the second frequency is shorter than a time period for applying the AC voltage having the first frequency, and
   wherein the time period for applying the AC voltage having the second frequency is from about 10 ms to 100 ms.

2. A microsphere measuring method in which an AC electric field is applied between a pair of electrodes immersed in a sample liquid containing microspheres contained in at least one of blood and saliva, the microspheres are placed at a predetermined position by a dielectrophoretic force, and a number of the microspheres in the sample liquid is measured, said method comprising:
   a step of applying an AC voltage having a first frequency between the pair of electrodes to cause a dielectrophoretic force to act on the microspheres;
   a step of applying an AC voltage having a second frequency between the pair of electrodes, the second frequency being used for measuring an impedance between the pair of electrodes, and the second frequency being higher than a frequency at which an influence of a Warburg impedance occurs, and
   a step of measuring the impedance between the pair of electrodes; and
   a step of calculating a time change of the impedance between the pair of electrodes, and calculating a number of the microspheres in the cell.

3. The microsphere measuring method according to claim 2, comprising
   a step of selecting the first frequency and the second frequency based on a solution electric conductivity.

4. The microsphere measuring method according to claim 2, comprising:
   a step superimposing and applying the AC voltage of the first frequency and the AC voltage of the second frequency between the pair of electrodes; and
   a step of separating frequency components of the AC voltage of the second frequency from the superimposed AC voltages applied between the pair of electrodes, and measuring the impedance between the pair of electrodes.

5. The microsphere measuring method according to claim 4, wherein the superimposed AC voltage applied to the pair of electrodes causes a positive dielectrophoretic force acting on the microspheres.

6. The microsphere measuring method according to claim 2, wherein the first frequency and the second frequency are sequentially switched and a time period for applying the AC voltage of the second frequency is shorter than a time period for applying the AC voltage of the first frequency.

7. The microsphere measuring method according to claim 2, wherein the AC voltage having the first frequency has a first amplitude and the AC voltage having the second frequency has a second amplitude, the first amplitude being different from the second amplitude.

8. The microsphere measuring method according to claim 7, wherein the second amplitude is smaller than the first amplitude.

9. The microsphere measuring method according to claim 2, wherein the second frequency is higher than 800 kHz and lower than the first frequency.

10. The microsphere measuring method according to claim 2, wherein the first frequency is from about 1 MHz to 10 MHz and the second frequency is from about 10 kHz to 1 MHz.

11. The microsphere measuring method according to claim 2, wherein the first frequency is about 1 MHz and the second frequency is about 10 kHz.

12. The microsphere measuring method according to claim 2, wherein the pair of electrodes is formed on a same surface.

13. The microsphere measuring method according to claim 2, wherein the pair of electrodes is formed on a same surface of a substrate.

* * * * *